United States Patent
Dohil et al.

(10) Patent No.: US 10,537,528 B2
(45) Date of Patent: Jan. 21, 2020

(54) METHODS OF TREATING NON-ALCOHOLIC STEATOHEPATITIS (NASH) USING CYSTEAMINE COMPOUNDS

(71) Applicants: The Regents of the University of California, Oakland, CA (US); Horizon Orphan LLC, Lake Forest, IL (US)

(72) Inventors: Ranjan Dohil, San Diego, CA (US); Patrice Rioux, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/771,947

(22) PCT Filed: Nov. 16, 2016

(86) PCT No.: PCT/US2016/062294
§ 371 (c)(1),
(2) Date: Apr. 27, 2018

(87) PCT Pub. No.: WO2017/087532
PCT Pub. Date: May 26, 2017

(65) Prior Publication Data
US 2018/0338928 A1   Nov. 29, 2018

Related U.S. Application Data

(60) Provisional application No. 62/256,035, filed on Nov. 16, 2015.

(51) Int. Cl.
| | | |
|---|---|---|
| *A61K 9/50* | (2006.01) | |
| *A61K 9/28* | (2006.01) | |
| *A61K 31/145* | (2006.01) | |
| *A61P 1/16* | (2006.01) | |
| *A61K 9/48* | (2006.01) | |
| *A61K 45/06* | (2006.01) | |

(52) U.S. Cl.
CPC ............... *A61K 9/50* (2013.01); *A61K 9/28* (2013.01); *A61K 9/4808* (2013.01); *A61K 31/145* (2013.01); *A61K 45/06* (2013.01); *A61P 1/16* (2018.01)

(58) Field of Classification Search
CPC .... A61K 31/145; A61K 31/205; A61K 47/38; A61K 9/0053; A61K 9/4808; A61K 9/4833; A61K 9/4866; A61K 9/50; A61K 9/501; A61K 9/5015; A61K 9/5026; A61K 9/5084
See application file for complete search history.

(56) References Cited

U.S. PATENT DOCUMENTS

| | | |
|---|---|---|
| 4,324,743 A | 4/1982 | Feuer |
| 4,959,306 A | 9/1990 | Kameda |
| 5,668,117 A | 9/1997 | Shapiro |
| 6,331,316 B1 | 12/2001 | Ullah et al. |
| 6,794,414 B1 | 9/2004 | Steinman |
| 7,449,451 B2 | 11/2008 | Prasad et al. |
| 7,994,226 B2 | 8/2011 | Dohil et al. |
| 8,026,284 B2 | 9/2011 | Dohil et al. |
| 8,129,433 B2 | 3/2012 | Dohil et al. |
| 8,263,662 B2 | 9/2012 | Dohil et al. |
| 9,149,448 B2 | 10/2015 | Dohil |
| 2003/0157191 A1 | 8/2003 | Kil |
| 2003/0162747 A1 | 8/2003 | Kil |
| 2004/0033985 A1 | 2/2004 | Chi |
| 2004/0106591 A1 | 6/2004 | Pacioretty |
| 2005/0027015 A1 | 2/2005 | Chi et al. |
| 2005/0137125 A1 | 6/2005 | Chan et al. |
| 2005/0209441 A1 | 9/2005 | Lile |
| 2005/0245433 A1 | 11/2005 | Chan |
| 2006/0140906 A1 | 6/2006 | Chi |
| 2007/0078113 A1 | 4/2007 | Roth |
| 2007/0172514 A1 | 7/2007 | Chi et al. |
| 2009/0023632 A1 | 1/2009 | Adamson et al. |
| 2009/0076166 A1 | 3/2009 | Dohil et al. |
| 2013/0183351 A1* | 7/2013 | Dohil .................. A61K 9/4891 424/400 |
| 2014/0370085 A1* | 12/2014 | Powell ................. A61K 9/5026 424/458 |

OTHER PUBLICATIONS

Quiros-Tejeira et al. (hereafter, "Quiros"), "Risk for Nonalcoholic Fatty Liver Disease in Hispanic Youth with BMI greater than or Equal to 95th Percentile", Journal of Pediatric Gastroenterology and Nutrition, 44: 228-326, 2007. (Year: 2007).*

Neuschwander-Tetri (hereafter "Neuschwander"), "Clinical, Laboratory and Histological Associations in Adults with Nonalcoholic Fatty Liver Disease", Helpatology, Sep. 2010, 913-924. (Year: 2010).*

(Continued)

*Primary Examiner* — Audrea B Coniglio
(74) *Attorney, Agent, or Firm* — Gavrilovich, Dodd & Lindsey LLP

(57) ABSTRACT

The disclosure relates, in general, to treatment of fatty liver disorders comprising administering compositions comprising cysteamine or cystamine compositions. The disclosure provides administration of enterically coated cysteamine compositions to treat fatty liver disorders, such as non-alcoholic fatty liver disease (NAFLD) and non-alcoholic steatohepatitis (NASH).

27 Claims, 4 Drawing Sheets

(56) References Cited

OTHER PUBLICATIONS

Younossi et al., "A Novel Diagnostic Biomarker Panel for Obesity-Related Nonalcoholic Steatohepatitis (NASH)", Obes. Surg, 2008, 18:1430-1437). (Year: 2008).*
Moon, Kihwan, International Preliminary Report on Patentability, The International Bureau of WIPO, PCT/US2016/062294, dated May 31, 2018.
Neuschwander-Tetri et al., "Clinical, Laboratory and Histologicla Associations in Adults with Nonalcoholic Fatty Liver Disease," Hepatology, 2010, vol. 52, No. 3, pp. 913-924.
Quiros-Tejeira et al., "Risk for Nonalcoholic Fatty Liver Disease in Hispanic Youth with BMI greater than or equal to 95th Percentile," J. of Ped. Gastroenterol. and Nutr., 2007, vol. 44, pp. 228-236.
Younossi et al., "A Novel Diagnostic Biomarker Panel for Obesity-related Nonalcoholic Steatohepatitis (NASH)," Obes. Surg., 2008, vol. 18, pp. 1430-1437.
Young, Lee W., Written Opinion, PCT/US2016/062294, United States Patent & Trademark Office, dated Jan. 30, 2017.

\* cited by examiner

METHODS OF TREATING NON-ALCOHOLIC STEATOHEPATITIS (NASH) USING CYSTEAMINE COMPOUNDS

CROSS REFERENCE TO RELATED APPLICATIONS

This application is a U.S. National Stage Application filed under 35 U.S.C. § 371 and claims priority to International Application No. PCT/US2016/062294, filed Nov. 16, 2016, which application claims priority of U.S. Provisional Application No. 62/256,035, filed Nov. 16, 2015, the disclosures of each of which are incorporated herein by reference in their entirety.

FIELD OF THE INVENTION

The invention relates in general to compositions and methods to treat fatty liver disease using cysteamine compounds.

BACKGROUND

Fatty liver disease (or steatohepatitis) is often associated with excessive alcohol intake or obesity, but also has other causes such as metabolic deficiencies including insulin resistance and diabetes. Fatty liver results from triglyceride fat accumulation in vacuoles of the liver cells resulting in decreased liver function, and possibly leading to cirrhosis or hepatic cancer.

Non-alcoholic fatty liver disease (NAFLD) represents a spectrum of disease occurring in the absence of alcohol abuse and includes non-alcoholic steatohepatitis (NASH). A satisfactory treatment for fatty liver disease, such as NAFLD and NASH is not presently available.

SUMMARY

The disclosure provides a method of treating a patient suffering from fatty liver disease comprising measuring one or more markers of liver function; measuring resistin, adiponectin and/or cytokeratin 18 levels; determining if the patient's BMI is above the $97^{th}$ percentile for the patient's age; determining if the patient has lobular inflammation or portal inflammation; identifying a patient with (i) liver function and resistin, adiponectin and/or cytokeratin 18 levels characteristic of fatty liver disease, and (ii) lobular inflammation; and administering a therapeutically effective amount of a cysteamine salt or cystamine salt composition to the patient to obtain a plasma level of about 10-80 µmol of cysteamine in the plasma. In one embodiment, the fatty liver disease is selected from the group consisting of non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy. In another embodiment, the one or more markers of liver function are selected from the group consisting of alanine aminotransferase (ALT), alkaline phosphatase (ALP), aspartate aminotransferase (AST), gamma-glutamyl transpeptidase (GGT), triglycerides, and lipoproteins (e.g., LDL). In a further embodiment, an ALT level of about 60-150 units/liter is indicative of fatty liver disease. In yet another or further embodiment, an ALP level of about 150-250 units/liter is indicative of fatty liver disease. In yet another of further embodiment, an AST level of about 40-100 units/liter is indicative of fatty liver disease. In still another or further embodiment, a GGT level of 50-100 units/liter is indicative of fatty liver disease. In still another of further embodiment, a triglyceride level above 150 mg/dL and/or high LDL level is indicative of fatty liver disease. In yet another or further embodiment, a resistin level of greater than 8 ng/ml is indicative of fatty liver disease. In still yet another or further embodiment, an adiponectin level decreased by at least about 20% from age and sex matched normal subjects is indicative of fatty liver disease. In another or further embodiment, the patient's BMI is above the $97^{th}$ percentile for the patient's age and the patient weighs less than or equal to 65 kg. In yet another embodiment of any of the foregoing, the patient comprises a BMI above $97^{th}$ percentile for age and weighs less than 65 kg and has triglyceride levels associated with NASH. In still another embodiment of any of the foregoing, the cysteamine salt composition is an enterically coated composition. In a further embodiment, the cysteamine salt is cysteamine bitartrate. In still another or further embodiment, the cysteamine salt compositions comprise granules or tablets. In still a further embodiment, the cysteamine salt composition comprises (i) a core particle comprising a mixture of cysteamine bitartrate and a binder, and (ii) an enteric membrane surrounding the core particle; wherein the core particles have a distribution of particle sizes in a range of about 0.7 mm to about 2.8 mm; wherein the enteric membrane begins to dissolve within a pH range of about 4.5 to about 6.5; wherein the enteric membrane is present in an amount in a range of about 25% to about 35% by weight, based on the weight of the core particles; and wherein the pharmaceutical dosage form, upon administration in a capsule to fasted healthy normal subjects at 600 mg free cysteamine base, provides: (a) a mean $C_{max}$ upon oral dosing in a range of 2.3±0.6 mg/L or in a range of 80% to 125% thereof; (b) a mean AUC (0-∞) upon oral dosing in a range of 0.84±0.19 min*mg/L/mg or in a range of 80% to 125% thereof; and (c) a plasma cysteamine level of 10-80 µmol. In yet another embodiment, the cysteamine salt composition comprises (i) a core tablet comprising a mixture of cysteamine bitartrate and a binder, and (ii) an enteric membrane surrounding the tablet, wherein the thickness of the enteric coating increases from 70 µm to 115 µm relative to the cysteamine base dose from 50 mg to 300 mg, and/or wherein the enteric coating is present in an amount in a range of about 9 to about 15% by weight of the core tablet and wherein upon delivery to a fasted healthy normal subject at 600 mg free cysteamine base the dose provides a plasma cysteamine level of 10-80 µm. In yet another embodiment, the cystamine salt composition is an enterically coated composition. In a further embodiment, the cystamine salt compositions comprise granules or tablets. In still a further embodiment, the cystamine salt composition comprises (i) a core particle comprising a mixture of cystamine and a binder, and (ii) an enteric membrane surrounding the core particle; wherein the beads have a distribution of particle sizes in a range of about 0.7 mm to about 2.8 mm; wherein the enteric membrane begins to dissolve within a pH range of about 4.5 to about 6.5; wherein the enteric membrane is present in an amount in a range of about 25% to about 35% by weight, based on the weight of the core particles; and wherein the pharmaceutical dosage form, upon administration in a capsule to fasted healthy normal subjects at 600 mg free cystamine base, provides: (a) a mean $C_{max}$ upon oral dosing in a range of 2.3±0.6 mg/L or in a range of 80% to 125% thereof; (b) a mean AUC (0-∞) upon oral dosing in a range of 0.84±0.19 min*mg/L/mg or in a range of 80% to 125% thereof; and (c) a plasma cysteamine level of 10-80 μmol. In yet another embodiment, the cystamine salt composition comprises (i) a core tablet comprising a mixture of cystamine and a binder, and (ii) an enteric membrane surrounding the core tablet, wherein the thickness of the enteric coating increases from 60 μm to 130 μm relative to the cystamine dose from 50 mg to 300 mg, and/or wherein the enteric coating is present in an amount in a range of about 9 to about 15% by weight of the core tablet and wherein upon delivery to a fasted healthy normal subject at 600 mg cystamine the dose provides a plasma cysteamine level of 10-80 μm.

The disclosure provides a method of treating a subject having Non-alcoholic steatohepatitis (NASH) and having lobular inflammation with little to no portal inflammation with a cysteamine or cystamine composition. In one embodiment, the subject comprises a BMI that is greater than $97^{th}$ percentile for the patient's age group. In a further embodiment, the subject is less than 65 kg. In still another embodiment of any of the foregoing the total daily dose of cysteamine or cystamine composition is about 0.5-2.0 g/m². In yet another embodiment of any of the foregoing, the total daily dose of cysteamine or cystamine composition is about 0.5-1.0 g/m². In yet another embodiment of any of the foregoing the composition is administered at a frequency of 4 or less times per day. In still yet another embodiment of any of the foregoing, the composition is administered two times per day. In still yet a further embodiment of any of the foregoing the composition is a delayed and extended release dosage form that provides increased delivery of the cysteamine or cystamine composition to the small intestine. In yet a further embodiment, the delayed and extended release dosage form provides a $C_{max}$ of the cysteamine or cysteamine derivative, or a biologically active metabolite thereof, that is at least about 35% higher than the $C_{max}$ provided by an immediate release dosage form containing the same amount of the cysteamine or cysteamine derivative. In yet another embodiment, the delayed and extended release dosage form provides a $C_{max}$ at least about 50% higher than the $C_{max}$ of the immediate release dosage form. In still another embodiment, the delayed and extended release dosage form provides a $C_{max}$ up to about 75% higher than the $C_{max}$ of the immediate release dosage form. In yet another embodiment, the delayed and extended release dosage form comprises an enteric coating that releases the cysteamine or cystamine composition when the composition reaches the small intestine or a region of the gastrointestinal tract of a subject in which the pH is greater than about pH 4.5. In yet a further embodiment, the composition comprises a coating selected from the group consisting of polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters.

In yet some other alternative embodiments of any of the foregoing, the administering results in improvement in liver fibrosis compared to levels before administration of the cysteamine or cystamine composition. In yet other embodiments of any of the foregoing, the administering results in a reduction in fat content of liver. In another embodiment of any of the foregoing the administering results in a reduction in the incidence of or progression of cirrhosis. In yet another embodiment of the foregoing embodiments the administering results in a reduction in the incidence of hepatocellular carcinoma. In still yet another embodiment of any of the foregoing the administering results in a decrease in hepatic aminotransferase levels compared to levels before administration of the cysteamine or cystamine composition. In still another embodiment, the administering results in a reduction in hepatic transaminase of between approximately 10% to 40% compared to levels before treatment. In yet other embodiments of the foregoing the administering results in a reduction in alanine aminotransferase levels in a treated patient to approximately 30%, 20% or 10% above normal ALT levels, or at normal ALT levels (≥40 iu/L). In yet another embodiment of any of the foregoing the administering results in a reduction in aspartate aminotransferase levels in a treated patient to approximately 30%, 20% or 10% above normal AST levels or to normal AST levels. In still yet more embodiments of any of the foregoing embodiments, the administering results in a reduction in serum ferritin levels compared to levels before treatment with the cysteamine or cystamine composition. In yet another embodiment of any of the foregoing the cysteamine or cystamine is administered with a second agent useful to treat fatty liver disease. In a further embodiment, the second agent is selected from a statin, a metformin, an antibody against oxidized phospholipids and any combination thereof.

The disclosure provides a method of treating a subject suffering from fatty liver disease comprising administering a therapeutically effective amount of a cysteamine composition. In one embodiment, the fatty liver disease is selected from the group consisting of non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy. In another embodiment, the total daily dose of cysteamine composition is about 0.5-2.0 g/m². In yet another embodiment, the cysteamine composition is administered at a frequency of 4 or less times per day (e.g., one, two or three times per day). In one embodiment, the composition is a delayed or controlled release dosage form that provides increased delivery of the cysteamine or cysteamine derivative to the small intestine. The delay or controlled release form can provide a $C_{max}$ of the cysteamine or cysteamine derivative, or a biologically active metabolite thereof, that is at least about 35%, 50%, 75% or higher than the $C_{max}$ provided by an immediate release dosage form containing the same amount of the cysteamine or cysteamine derivative. In yet another embodiment, the delayed or controlled release dosage form comprises an enteric coating that releases the cysteamine composition when the composition reaches the small intestine or a region of the gastrointestinal tract of a subject in which the pH is greater than about pH 4.5. For example, the coating can be selected from the group consisting of polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters. The composition can be administered orally or parenterally. In another embodiment, the method results in improvement in liver fibrosis compared to levels before administration of the cysteamine composition. In yet another embodiment, the method results in a reduction in fat content of liver, a reduction in the incidence of or progression of cirrhosis, or a reduction in the incidence of hepatocellular carcinoma. In one embodiment, the method results in a decrease in hepatic aminotransferase levels compared to levels before administration of the cysteamine composition. In a further embodiment, the administering results in a reduction in hepatic transaminase of between approximately 10% to 40% compared to levels before treatment. In yet another embodiment, the administering results in a reduction in alanine or aspartate aminotransferase levels in a treated patient to approximately 30%, 20% or 10% above normal ALT levels, or at normal ALT levels. In yet other embodiment, the administering results in a reduction in serum ferritin levels compared to levels before treatment with the cysteamine composition. The methods and composition of the disclosure can also include administering a second agent in combination with a cysteamine composition to treat fatty liver disease. The subject can be an adult, adolescent or child.

In one embodiment, the disclosure provides a method of treating a patient suffering from fatty liver disease, including NAFLD or NASH, comprising administering a therapeutically effective amount of a composition comprising a cysteamine or cystamine composition. The methods of the disclosure also include use of a cysteamine or cystamine composition in preparation of a medicament for treatment of fatty liver disease, and use of a cysteamine or cystamine composition in preparation of a medicament for administration in combination with a second agent for treating fatty liver disease. Also included is use of a second agent for treating fatty liver disease in preparation of a medicament for administration in combination with a cysteamine or cystamine composition. Further provided are kits comprising a cysteamine or cystamine composition for treatment of fatty liver disease, optionally with a second agent for treating fatty liver disease, and instructions for use in treatment of fatty liver disease. The term "fatty liver disease" may include or exclude NASH.

DETAILED DESCRIPTION

Figure 1:
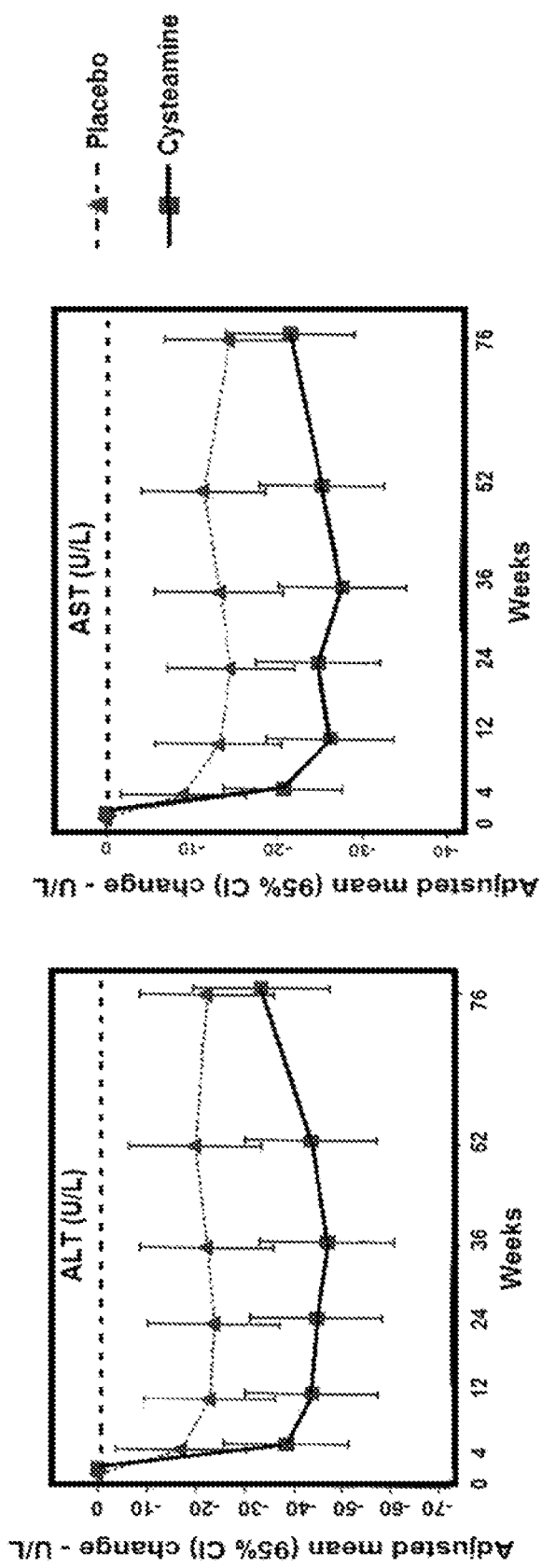
FIG. 1 shows changes from baseline in liver enzymes, total cholesterol, HOMA-IR, BMI and BMI z-score according to treatment group, adjusted for baseline value.
Figure 1:
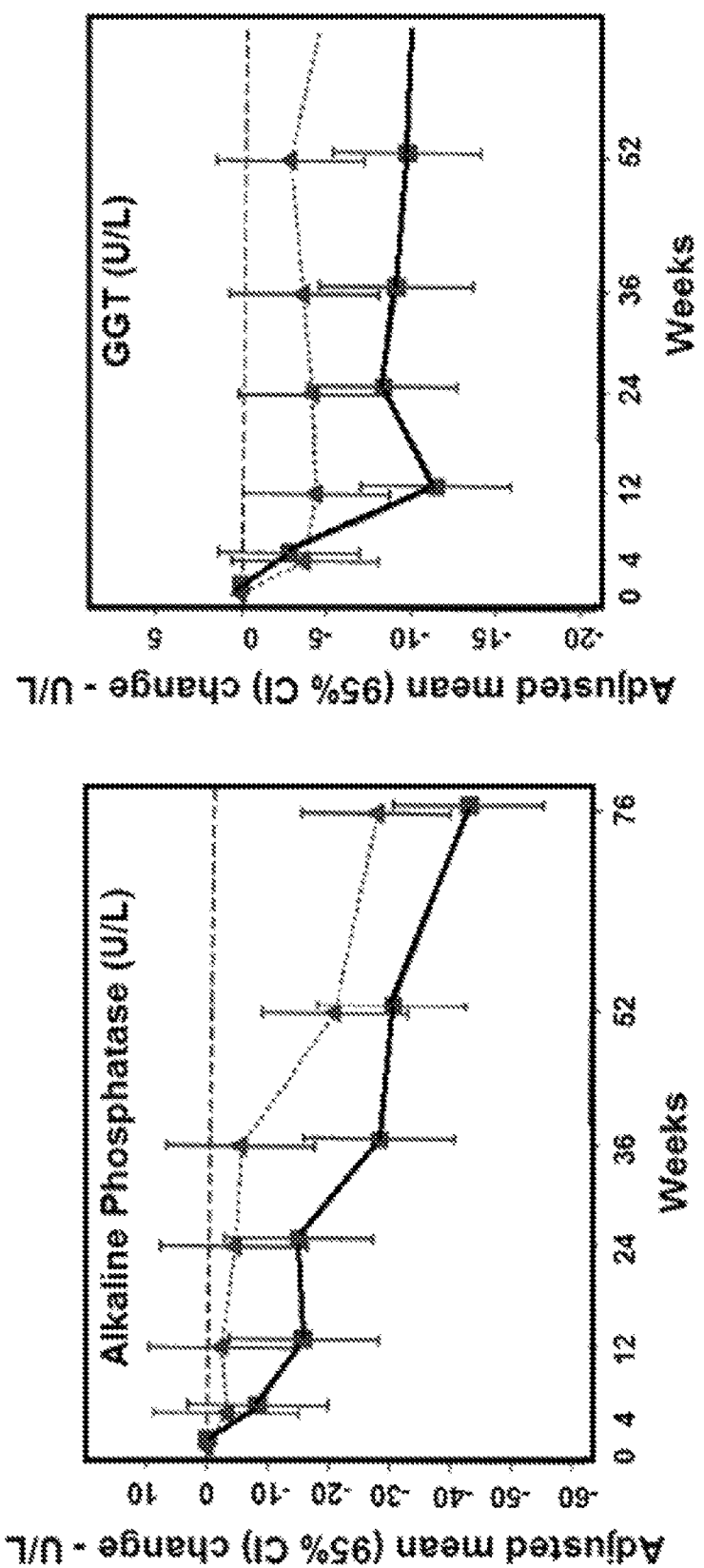
Figure 1:
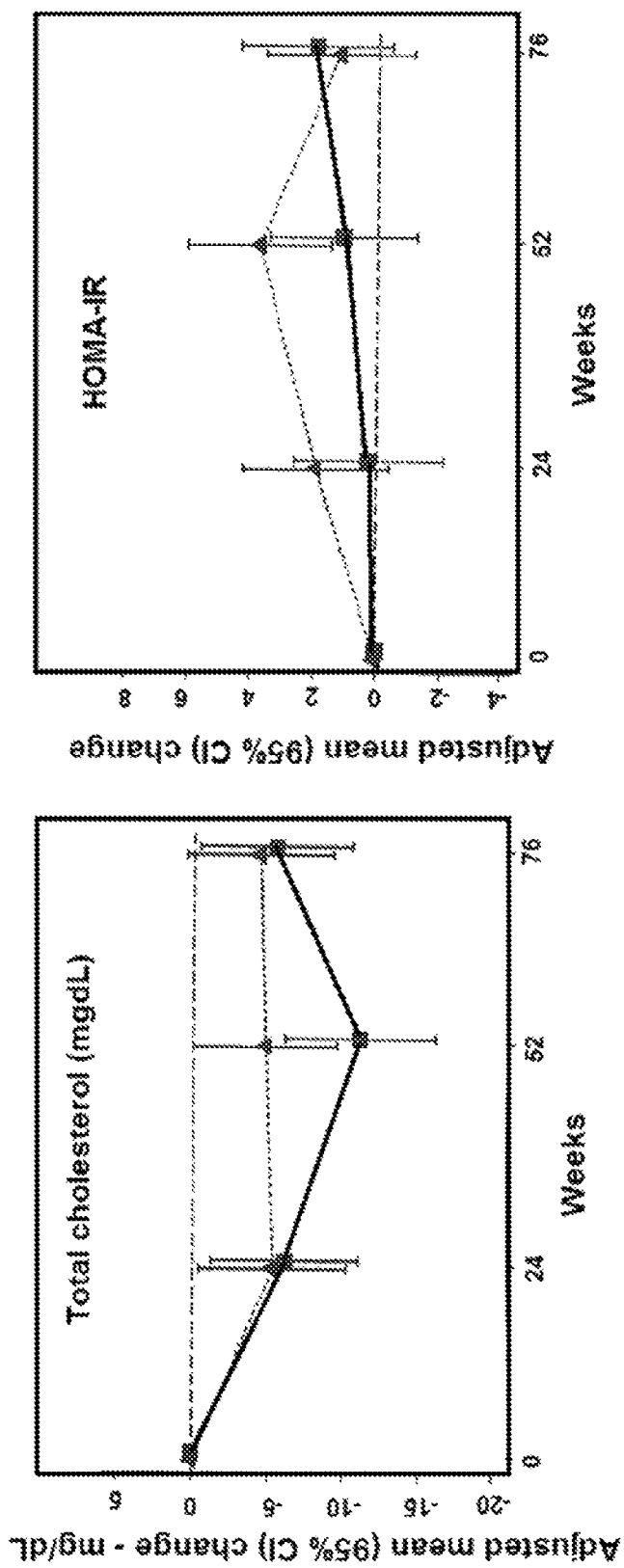
Figure 1:
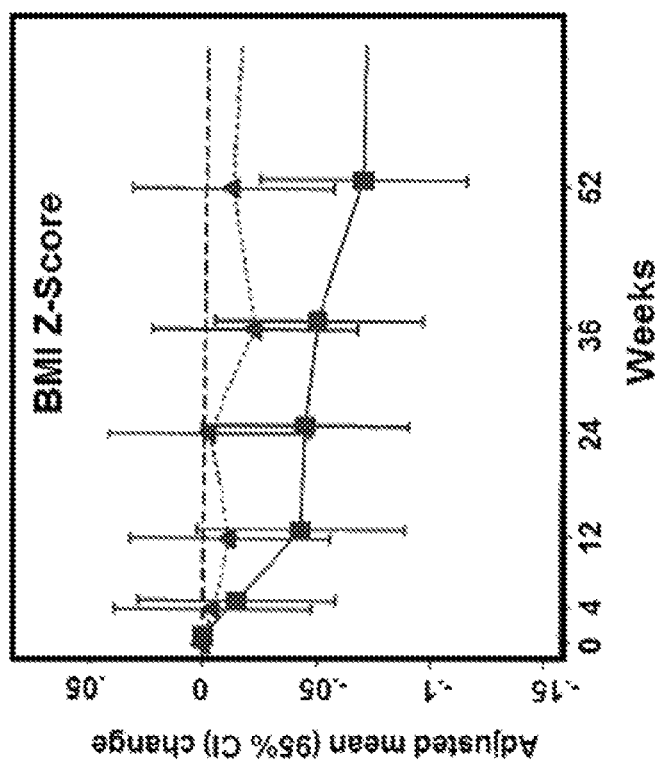
Figure 1:
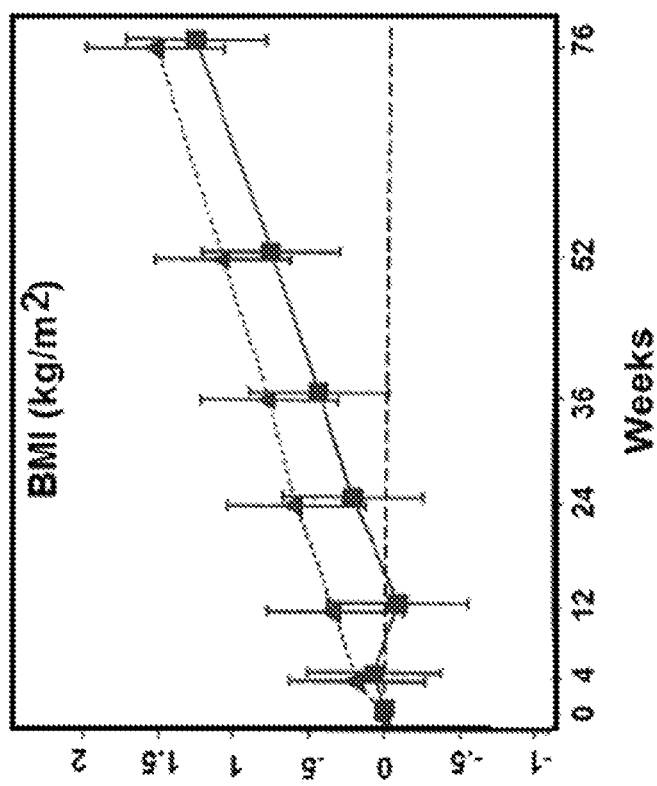

As used herein and in the appended claims, the singular forms "a," "and" and "the" include plural referents unless the context clearly dictates otherwise. Thus, for example, reference to "a derivative" includes a plurality of such derivatives and reference to "a subject" includes reference to one or more subjects and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "substantially" as used herein refers to a majority of, or mostly, as in at least about 51%, 60%, 70%, 80%, 90%, 95%, 96%, 97%, 98%, 99%, 99.5%, 99.9%, 99.99%, or at least about 99.999% or more.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Cysteamine is a small aminothiol molecule that is easily transported across cellular membranes. Cysteamine markedly reduces intralysosomal cysteine accumulation and is currently approved as a treatment for cystinosis. Cysteamine can increase the cellular thiol and free thiol tripeptide glutathione pool, and thus modulate reactive oxygen species (ROS) scavenging, and decreased lipoperoxidation and glutathione peroxidase activity. Furthermore, cysteamine also increases adiponectin levels.

Cysteamine is an attractive candidate for the treatment of NASH, as it reacts with cystine to produce cysteine, which can further be metabolized into glutathione, a potent endogenous antioxidant. Cysteamine is a precursor to the protein glutathione (GSH) precursor, and is currently FDA approved for use in the treatment of cystinosis, an intra-lysosomal cystine storage disorder. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Within the cytosol the mixed disulfide can be reduced by its reaction with glutathione and the cysteine released can be used for further GSH syntheses. The synthesis of GSH from cysteine is catalyzed by two enzymes, gamma-glutamylcysteine synthetase and GSH synthetase. This pathway occurs in almost all cell types, with the liver being the major producer and exporter of GSH. The reduced cysteine-cysteamine mixed disulfide will also release cysteamine, which, in theory is then able to re-enter the lysosome, bind more cystine and repeat the process (Dohil et al., J Pediatr 2006; 148(6):764-9). In a recent study in children with cystinosis, enteral administration of cysteamine resulted in increased cysteamine absorption, which subsequently caused prolonged efficacy in the lowering of leukocyte cystine levels (Dohil et al., J Pediatr 2006; 148(6):764-9). This may have been due to "re-cycling" of cysteamine when adequate amounts of drug reached the lysosome. If cysteamine acts in this fashion, then GSH production may also be significantly enhanced.

Cysteamine is a potent gastric acid-secretagogue that has been used in laboratory animals to induce duodenal ulceration. Studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2 to 3-fold rise in gastric acid-hypersecretion, and a 50% rise in serum gastrin levels. Symptoms suffered by these individuals included abdominal pain, heartburn, nausea, vomiting, and anorexia. U.S. patent application Ser. No. 11/990,869 and published International Publication No. WO 2007/089670, both claiming priority to U.S. Provisional Patent application No. 60/762,715, filed Jan. 26, 2006, (all of which are incorporated by reference herein in their entirety) showed that cysteamine induced hypergastrinemia arises, in part, as a local effect on the gastric antral-predominant G-cells in susceptible individuals. The data also suggest that this is also a systemic effect of gastrin release by cysteamine. Depending on the route of administration, plasma gastrin levels usually peak after intragastric delivery within 30 minutes whereas the plasma cysteamine levels peak later.

In addition, sulfhydryl (SH) compounds such as cysteamine, cystamine, and glutathione are among the most important and active intracellular antioxidants. Cysteamine protects animals against bone marrow and gastrointestinal radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. The protection is thought to result from scavenging of free radicals, either directly or via release of protein-bound GSH. An enzyme that liberates cysteamine from coenzyme A has been reported in avian liver and hog kidney. Recently, studies have appeared demonstrating a protective effect of cysteamine against the hepatotoxic agents acetaminophen, bromobenzene, and phalloidine.

Cystamine, in addition, to its role as a radioprotectant, has been found to alleviate tremors and prolong life in mice with the gene mutation for Huntington's disease (HD). The drug may work by increasing the activity of proteins that protect nerve cells, or neurons, from degeneration. Cystamine appears to inactivate an enzyme called transglutaminase and thus results in a reduction of huntingtin protein (Nature Medicine 8, 143-149, 2002). In addition, cystamine was found to increase the levels of certain neuroprotective proteins. However, due to the current methods and formulation of delivery of cystamine, degradation and poor uptake require excessive dosing.

At present, cysteamine is FDA approved only for the treatment of cystinosis. Patients with cystinosis are normally required to take cysteamine every 6 hours or use an enteric form of cysteamine (e.g., PROCYSBI®) every 12 hours.

The disclosure is not limited with respect to a specific cysteamine or cystamine salt or ester or derivative; the compositions of the disclosure can contain any cysteamine or cystamine, cysteamine or cystamine derivative, or combination of cysteamine or cystamines. The active agents in the composition, i.e., cysteamine or cystamine, may be administered in the form of a pharmacologically acceptable salt, ester, amide, prodrug or analog or as a combination thereof. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

Subjects with cystinosis are required to ingest oral cysteamine (CYSTAGON®) every 6 hours day and night or use an enteric form of cysteamine (PROCYSBI®) every 12 hours. When taken regularly, cysteamine can deplete intracellular cystine by up to 90% (as measured in circulating white blood cells), and reduces the rate of progression to kidney failure/transplantation and also to obviate the need for thyroid replacement therapy. Because of the difficulty in taking CYSTAGON®, reducing the required dosing improves the adherence to therapeutic regimen. International Publication No. WO 2007/089670 demonstrates that delivery of cysteamine to the small intestine reduces gastric distress and ulceration, increases $C_{max}$ and increases AUC. Delivery of cysteamine into the small intestine is useful due to improved absorption rates from the small intestine, and/or less cysteamine undergoing hepatic first pass elimination when absorbed through the small intestine. A decrease in leukocyte cystine was observed within an hour of treatment.

A pilot trial by Dohil et al. in 11 children with biopsy-confirmed NAFLD received enteric-coated (EC) cysteamine bitartrate orally for 24 weeks. This therapy resulted in statistically significant reductions in mean serum levels of ALT, aspartate aminotransferase (AST), total adiponectin, leptin, and cytokeratin-18 fragments, but without a concomitant reduction in body mass index. Seven out of 11 subjects reached the primary endpoints (of at least 50% reduction in ALT). The reduction in mean ALT and AST levels persisted 16 weeks after treatment ended.

However, Schwimmer et al. (Hepatology, 62(6):1398A-1399A, December 2015) indicated that after one year of treatment with delayed released cysteamine bitartrate the therapy was safe, but did not improve liver histology. Although there was substantial and rapid improvements in liver enzymes with the delayed release cysteamine bitartrate.

This disclosure identifies patient populations that can benefit from cysteamine therapy, particularly juvenile patients, whose progression from NAFLD to NASH may be treated and/or prevented. The disclosure also provides composition of cysteamine and cystamine that can be used in the treatment of various diseases including cystinosis, Huntington's disease, and NAFLD (including NASH).

Non-alcoholic fatty liver disease (NAFLD) represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). NAFLD is linked to insulin resistance, it causes liver disease in adults and children and may ultimately lead to cirrhosis (Skelly et al., J Hepatol 2001; 35: 195-9; Chitturi et al., Hepatology 2002; 35(2):373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl: S186-90). NASH is characterized by the histologic presence of steatosis, cytological ballooning, scattered inflammation and pericellular fibrosis (Contos et al., Adv Anat Pathol 2002; 9:37-51). Hepatic fibrosis resulting from NASH may progress to cirrhosis of the liver or liver failure, and in some instances may lead to hepatocellular carcinoma.

The degree of insulin resistance (and hyperinsulinemia) correlates with the severity of NAFLD, being more pronounced in patients with NASH than with simple fatty liver (Sanyal et al., Gastroenterology 2001; 120(5):1183-92). As a result, insulin-mediated suppression of lipolysis occurs and levels of circulating fatty acids increase. Two factors associated with NASH include insulin resistance and increased delivery of free fatty acids to the liver. Insulin blocks mitochondrial fatty acid oxidation. The increased generation of free fatty acids for hepatic re-esterification and oxidation results in accumulation of intrahepatic fat and increases the liver's vulnerability to secondary insults.

Glutathione (gammaglutamyl-cysteinyl-glycine; GSH) is a major endogenous antioxidant and its depletion is implicated in the development of hepatocellular injury (Wu et al., J Nutr 2004; 134(3):489-92). One such injury is acetaminophen poisoning, where reduced GSH levels become depleted in an attempt to conjugate and inactivate the hepatotoxic metabolite of the drug. After a toxic dose of acetaminophen, excess metabolite (N-acetyl-benzoquinoneimine) covalently binds to hepatic proteins and enzymes resulting in liver damage (Wu et al., J Nutr 2004; 134(3):489-92; Prescott et al., Annu Rev Pharmacol Toxicol 1983; 23:87-101). Increased glutathione levels appears therefore to have some protective effects through the reduction of ROS. Glutathione itself is does not enter easily into cells, even when given in large amounts. However, glutathione precursors do enter into cells and some GSH precursors such as N-acetylcysteine have been shown to be effective in the treatment of conditions such as acetaminophen toxicity by slowing or preventing GSH depletion (Prescott et al., Annu Rev Pharmacol Toxicol 1983; 23:87-101). Examples of GSH precursors include cysteine, N-acetylcysteine, methionine and other sulphur-containing compounds such as cysteamine (Prescott et al., J Int Med Res 1976; 4(4 Suppl):112-7).

Cysteine is a major limiting factor for GSH synthesis and that factors (e.g., insulin and growth factors) that stimulate cysteine uptake by cells generally result in increased intracellular GSH levels (Lyons et al., Proc Natl Acad Sci USA 2000; 97(10):5071-6; Lu S C. Curr Top Cell Regul 2000; 36:95-11).

N-acetylcysteine has been administered to patients with NASH. In reports from Turkey, obese individuals with NASH treated with N-acetylcysteine for 4-12 weeks exhibited an improvement in aminotransferase levels and gamma-GT even though there was no reported change in subject body mass index (Pamuk et al., J Gastroenterol Hepatol 2003; 18(10):1220-1).

Studies in mice and humans showed cysteamine to be effective in preventing acetaminophen-induced hepatocellular injury (Prescott et al., Lancet 1972; 2(7778):652; Prescott et al., Br Med J 1978; 1(6116):856-7; Mitchell et al., Clin Pharmacol Ther 1974; 16(4):676-84). Cystamine and cysteine have been reported to reduce liver cell necrosis induced by several hepatotoxins. (Toxicol Appl Pharmacol. 1979 April; 48(2):221-8). Cystamine has been shown to ameliorate liver fibrosis induced by carbon tetrachloride via inhibition of tissue transglutaminase (Qiu et al., World J Gastroenterol. 13:4328-32, 2007).

The prevalence of NAFLD in children is unknown because of the requirement of histologic analysis of liver in order to confirm the diagnosis (Schwimmer et al., Pediatrics 2006; 118(4):1388-93). However, estimates of prevalence can be inferred from pediatric obesity data using hepatic ultra-sonongraphy and elevated serum transaminase levels and the knowledge that 85% of children with NAFLD are obese. Data from the National Health and Nutrition Examination Survey has revealed a threefold rise in the prevalence of childhood and adolescent obesity over the past 35 years; data from 2000 suggests that 14-16% children between 6-19 yrs age are obese with a BMI >95% (Fishbein et al., J Pediatr Gastroenterol Nutr 2003; 36(1):54-61), and also that fact that 85% of children with NAFLD are obese.

The exact mechanism by which NAFLD develops into NASH remains unclear. Because insulin resistance is associated with both NAFLD and NASH, it is postulated that other additional factors are also required for NASH to arise. This is referred to as the "two-hit" hypothesis (Day C P. Best Pract Res Clin Gastroenterol 2002; 16(5):663-78) and involves, firstly, an accumulation of fat within the liver and, secondly, the presence of large amounts of free radicals with increased oxidative stress. Macrovesicular steatosis represents hepatic accumulation of triglycerides, and this in turn is due to an imbalance between the delivery and utilization of free fatty acids to the liver. During periods of increased calorie intake, triglyceride will accumulate and act as a reserve energy source. When dietary calories are insufficient, stored triglycerides (in adipose) undergo lipolysis and fatty acids are released into the circulation and are taken up by the liver. Oxidation of fatty acids will yield energy for utilization. Treatment of NASH currently revolves around the reduction of the two main pathogenetic factors, namely, fat accumulation within the liver and excessive accumulation of free radicals causing oxidative stress. Fat accumulation is diminished by reducing fat intake as well as increasing caloric expenditure. One therapeutic approach is sustained and steady weight loss. Although not definitively proven, a >10% loss in body weight has been shown in some cases to reduce hepatic fat accumulation, normalize liver transaminases and improve hepatic inflammation and fibrosis (Ueno et al., J Hepatol 1997; 27(1):103-7; Vajro et al., J Pediatr 1994; 125(2):239-41; Franzese et al., Dig Dis Sci 1997; 42(7):1428-32).

Reduction of oxidative stress through treatment with antioxidants has also been shown to be effective in some studies. For example, obese children who had steatosis were treated with vitamin E (400-1000 IU/day) for 4-10 months (Lavine J Pediatr 2000; 136(6):734-8). Despite any significant change in BMI, the mean ALT levels decreased from 175±106 IU/L to 40±26 IU/L (P<0.01) and mean AST levels decreased from 104±61 IU/L to 33±11 IU/L (P<0.002). Hepatic transaminases increased in those patients who elected to discontinue vitamin E therapy. An adult study using vitamin E for one year demonstrated similar reduction of hepatic transaminases as well as the fibrosis marker TGFβ levels (Hasegawa et al., Aliment Pharmacol Ther 2001; 15(10):1667-72).

Steatosis also may develop into steatohepatitis through oxidative stress due to reactive oxygen species (ROS) and decreased anti-oxidant defense (Sanyal et al., Gastroenterology 2001; 120(5):1183-92). ROS can be generated in the liver through several pathways including mitochondria, peroxisomes, cytochrome P450, NADPH oxidase and lipooxygenase (Sanyal et al., Nat Clin Pract Gastroenterol Hepatol 2005; 2(1):46-53). Insulin resistance and hyperinsulinism has been shown to increase hepatic oxidative stress and lipid peroxidation through increased hepatic CYP2EI activity (Robertson et al., Am J Physiol Gastrointest Liver Physiol 2001; 281(5):G1135-9; Leclercq et al., J Clin Invest 2000; 105(8):1067-75).

Currently, much of what is understood of the pathogenesis of NAFLD has arisen from animal studies. A number of mouse models which exhibit steatosis/steatohepatitis exist and include genetically altered leptin-deficient (ob/ob) or leptin resistant (db/db) and the dietary methionine/choline deficient (MCD) model. Studies comparing male and female rats of varying strains (Wistar, Sprague-Dawley, Long-Evans) with a mouse strain (C57BL/6) as models for NASH have been undertaken. These animals were fed for 4 weeks with an MCD diet; although ALT elevation and steatosis were more noticeable in the Wistar rat, the overall histologic changes in the liver of the mice were more constant with changes due to NASH. More recently the use of supra-nutritional diets in animals has resulted in a NAFLD model that physiologically more resembles the human phenotype. The medical conditions most commonly associated with NAFLD are obesity, Type II diabetes and dyslipidemia. These conditions can be induced by feeding mice and rats with high fat or sucrose diets. Rats fed with a >70% fat-rich diet for 3 weeks developed pan-lobular steatosis, patchy inflammation, enhanced oxidative stress, and increased plasma insulin concentrations suggesting insulin resistance. NASH mice have been induced through intragastric overfeeding. Mice were fed up to 85% in excess of their standard intake for 9 weeks. The mice became obese with 71% increase in final body weight; they demonstrated increase white adipose tissue, hyperglycemia, hyperinsulinemia, hyperleptinemia, glucose intolerance and insulin resistance. Of these mice 46% developed increased ALT (121=/−27 vs 13+/−1 U/L) as well as histologic features suggestive of NASH. The livers of the overfed mice were about twice as large expected, beige in color with microscopic evidence of lipid droplets, cytoplasmic vacuoles and clusters of inflammation.

Mouse models of NASH can be used to study various therapies. Mouse models are created through specific diets (methionine choline deficient, MCD) or intragastric overfeeding. These mice develop serologic and histologic features of NASH. NASH mice are useful in screening and measuring the effects cysteamine on NASH related disease and disorders. For example, the effect of treatment can be measured by separating the NASH mice into a control group where animals will continue to receive MCD diet only and three other treatment groups where mice will receive MCD diet as well as anti-oxidant therapy. The three therapy groups for example, can receive cysteamine 50 mg/kg/day, 100 mg/kg/day and sAME.

As mentioned above, NASH is a disease subset falling under the umbrella of NAFLD and is characterized by various biomarkers and histological examination. NASH has been characterized as including two types: Type 1 and Type 2, having some distinct biomarker and histological characteristics, while certain others that overlap between the two types. These two types, Type 1 and Type 2 NASH are typically identified in juvenile patients.

Type 1 NASH is characterized by steatosis, lobular inflammation, ballooning degeneration and perisinusoidal fibrosis. Type 2 NASH is characterized by steatosis, portal inflammation, and portal fibrosis. Schwimmer et al. (Hepatgology, 42(3):641-649, 2005; incorporated herein by reference) described various criteria and biomarkers used to differentiate NASH Type 1 from NASH Type 2. In particular, Schwimmer et al. discloses that subjects with NASH Type 1 had higher AST, ALT and triglyceride levels compared to patients with NASH Type 2. However, the strongest factor demonstrating a difference in the two types of NASH are best found upon histological examination. As stated above, Type 1 NASH demonstrates a prevalent lobular inflammation in the liver in contrast with a prevalent portal inflammation in Type 2 NASH. Thus, the disclosure contemplates that one of the key differentiating factors that can be used in the methods disclosed herein is identifying, by histological examination, the presence of Type 1 vs. Type 2 NASH.

The diagnosis of steatosis is typically made when lipid deposition is visible in more than 5% of hepatocytes. NASH is diagnosed when, in addition to hepatic steatosis, both inflammatory infiltrates as well as ballooning and liver cell injury are present. The NAFLD Activity Score (NAS) was developed to provide a numerical score for patients who most likely have NASH. Accordingly, the NAS is the sum of the separate scores for steatosis (0-3), hepatocellular ballooning (0-2) and lobular inflammation (0-3), with the majority of patients with NASH having a NAS score of ≥5 (Kleiner D E, Brunt E M, Van Natta M et al. Design and validation of a histological scoring system for nonalcoholic fatty liver disease. Hepatology 41(6), 1313-1321 (2005)).

In addition, various studies have shown that cytokeratin 18 is a useful indicator of inflammation in NASH, due to cytokeratin 18's release from hepatocytes undergoing apoptosis. Normal cytokeratin 18 levels are typically characterized as being less than 200 units per liter. In contrast, subjects with liver disease, including NALFD and NASH have a statistically significant elevation in cytokeratin 18 (e.g., above 200 U/L; 200-300 U/L). Moreover, cytokeratin 18 levels can be used as a marker to determine whether a treatment is being effective. For example, a reduction in cytokeratin 18 levels of greater than 10% (e.g., 20-30%, 30-40%, 40-50%, 50-60%, 60-70%, 70-80% or 90-100%) is indicative that the therapy is having a beneficial effect. Other markers include commonly used liver function tests including measuring one or more of, for example, serum alanine aminotransferase (ALT), alkaline phosphatase (ALP), aspartate aminotransferase (AST) and gamma-glutamyl transpeptidase (GGT).

In patients with histologically proven NAFLD, serum hepatic aminotransferases, specifically alanine aminotransferase (ALT), levels are elevated from the upper limit of normal to 10 times this level (Schwimmer et al., J Pediatr 2003; 143(4):500-5; Rashid et al., J Pediatr Gastroenterol Nutr 2000; 30(1):48-53). The ratio of ALT/AST (aspartate aminotransferase) is >1 (range 1.5-1.7) which differs from alcoholic steatohepatitis where the ratio is generally <1. Other abnormal serologic tests that may be abnormally elevated in NASH include gamma-glutamyltransferase (gamma-GT) and fasting levels of plasma insulin, cholesterol and triglyceride.

ALT levels have been shown to be indicative of liver function. For example, normal ALT levels are about 7 to 55 units (e.g., 10-40 units) per liter has been shown to correlate with normal liver function. This value is somewhat varied in children and adolescents. Thus, in some instances ALT levels less than 25 units per liter are "normal" in children and adolescents. Increased levels of ALT have been shown to correlate with liver disease and disorders. For example, NAFLD and NASH subjects typically show ALT levels of between 60 to 150 (e.g., 60-145, 70-140, 80-135, 90-130, 105-125, 110-120, or any number between any two values thereof). In some embodiment, particularly with children and adolescents, ALT levels above 25 units per liter can be indicative of NASH or NAFLD. In determining if a subject has NAFLD or NASH or is susceptible to treatment using a cysteamine or cystamine composition, ALT may be measured alone, but preferably, the determination should be made in combination with one or more other markers of liver function or dysfunction. For example, a subject having ALT levels above about 80 is indicative of liver disease or dysfunction.

AST levels have been shown to be indicative of liver function. For example, AST levels between about 8 to 48 units (e.g., 10-40 units) per liter has been shown to correlate with normal liver function. Increased levels of AST have been shown to correlate with liver disease and disorders. For example, NAFLD and NASH subjects typically show AST levels of between 40 to 100 (e.g., 45-95, 55-90, 65-85, 70-80, or any number between any two values thereof). In determining if a subject has NAFLD or NASH or is susceptible to treatment using a cysteamine or cystamine composition, AST may be measured alone, but preferably the determination should be made in combination with one or more other markers of liver function or dysfunction. For example, a subject having AST levels above about 50 is indicative of liver disease or dysfunction.

ALP levels have been shown to be indicative of liver function. For example, ALP levels between about 45 to 115 units (e.g., 50-110 units) per liter has been shown to correlate with normal liver function. Increased levels of ALP have been shown to correlate with liver disease and disorders. For example, NAFLD and NASH subjects typically show ALP levels of between 150 to 250 (e.g., 155-245, 160-240, 165-235, 170-230, 175-225, 180-220, 185-215, 190-210, 195-200, or any number between any two values thereof). In determining if a subject has NAFLD or NASH or is susceptible to treatment using a cysteamine or cystamine composition, ALP may be measured alone, but preferably the determination should be made in combination with one or more other markers of liver function or dysfunction. For example, a subject having ALP levels above about 150 is indicative of liver disease or dysfunction.

GGT levels have been shown to be indicative of liver function. For example, GGT levels between about 9 to 48 units (e.g., 10-40 units) per liter has been shown to correlate with normal liver function. Increased levels of GGT have been shown to correlate with liver disease and disorders. For example, NAFLD and NASH subjects typically show GGT levels of between 50 to 100 (e.g., 55-95, 60-90, 65-85, 70-80, or any number between any two values thereof). In determining if a subject has NAFLD or NASH or is susceptible to treatment using a cysteamine or cystamine composition, GGT may be measured alone, but preferably the determination should be made in combination with one or more other markers of liver function or dysfunction. For example, a subject having GGT levels above about 50 is indicative of liver disease or dysfunction.

Triglycerides levels have been shown to be indicative of liver function. For example, triglyceride levels less than about 150 mg/dL (e.g., 100-150 mg/dL) has been shown to correlate with normal liver function. Increased levels of triglycerides have been shown to correlate with liver disease and disorders. For example, NAFLD and NASH subjects typically show triglyceride levels of between 150 to 200 (e.g., 155-195, 160-190, 165-185, 170-180, or any number between any two values thereof). In determining if a subject has NAFLD or NASH or is susceptible to treatment using a cysteamine or cystamine composition, triglycerides may be measured alone, but preferably the determination should be made in combination with one or more other markers of liver function or dysfunction. For example, a subject having triglyceride levels above about 150 mg/dl is indicative of liver disease or dysfunction.

High triglyceride levels are known to be a leading cause of various forms of inflammation. Triglycerides are the form in which fat moves through the bloodstream. Triglycerides can be metabolized by various organs, including the liver, to form phospholipids (LDLs and HDLs), cholesterol and oxidized forms thereof. Oxidized phospholipids (OxPL) including OxLDL are known inflammatory mediators and strongly correlated with cardiovascular diseases. For example, Bieghs et al. (Hepatology, 65(3):894-903, 2012) describe that the use of antibodies to oxLDL led to a reduction in hepatic inflammation.

Increased amounts of adipose tissue are associated with decreased production of adiponectin. Data from studies in mice and humans increasingly implicate insufficient adiponectin as a major factor in the development of fatty liver and steatohepatitis. Adiponectin circulates as trimer (low molecular weight adiponectin), hexamer (medium molecular weight adiponectin) and higher order multimer (high molecular weight adiponectin) in serum and isoform-specific effects have been demonstrated. Epidemiological studies revealed that low adiponectin levels are associated with NASH. Moreover, adiponectin is believed to have a hepto-protective effect due to protective effects against oxidative damage. Normal levels of adiponectin vary by age and sex. For example, females have a higher baseline adiponectin level compared to males. A normal weight female typically has an adiponectin level of between about 8.5 and 11 µg/ml and males typically have an adiponectin level of between about 6 and 8 µg/ml. In contrast, subject with fatty liver disease, NASH and/or obesity have adiponectin levels that are about 50-90% of normal levels (e.g., decreased by 10-50% from normal, or any value there between) (see, e.g., Merl et al. Int. J. Obes (Lond), 29(8):998-1001, 2005).

In contrast, the resistin protein is increased in NASH subjects compared to normal subjects. Human resistin is a cysteine-rich, 108-amino-acid peptide hormone with a molecular weight of 12.5 kDa. In adult humans, resistin is expressed in bone marrow. Moreover in adipocytes of subjects having a low or healthy BMI, resistin mRNA is almost undetectable. Consistent with this, body mass index (BMI) is appears to correlate with resistin concentrations in serum, and women may have higher resistin concentrations than men. Resistin mRNA expression in human peripheral mononuclear cells is increased by proinflammatory cytokines. Serum resistin is significantly elevated in both NASH and simple steatotic subjects. Hepatic resistin is significantly increased in NASH patients in both mRNA and protein levels than those in simple steatosis and normal control subjects. Because of the cysteine-rich structure of resistin changes in sulfur availability (mainly due to cysteine and glutathione) can have an effect on the protein's structure and function. As mentioned above, cysteamine and cystamine can modulated cysteine and/or glutathione levels in subjects taking cysteamine or cystamine.

Subjects afflicted with NAFLD or NASH tend to be in a higher percentile of weight for their age group (e.g., above the 97$^{th}$ percentile for BMI for their age group). Treating pediatric patients at an early stage may have lifelong benefits in the management of liver function and obesity.

The disclosure provides populations of subject with NASH that that have high probability of responding to treatment with a cysteamine or cystamine composition. The disclosure provides a method of treating a subject suffering from fatty liver disease, such as NASH, comprising administering a therapeutically effective amount of a cysteamine or cystamine composition. In one embodiment, the fatty liver disease is selected from the group consisting of non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

In certain embodiments described more fully below, pediatric and juvenile patients are treated. In one embodiment, a subject having NASH is administered an enterically coated cysteamine or cystamine composition in an amount to obtain about 10-80 μmol (e.g., 10, 20, 30, 40, 50, 60, 70, 80 or any value there between) of cysteamine in the plasma. In one embodiment, the dose is about 10-40 mg/kg. In another embodiment, the dose is administered 2-4 times per day at about 300 mg to 1 gram per dose. Typically, the dose is changed over time to reach the highest tolerable dose for the subject, typically between about 30-50 μmol plasma cysteamine. For example, an initial dose may provide a circulating level of about 10 μmol cysteamine, which will be adjusted up to the highest tolerable dose, typically about 40 μmol. Similarly, an initial dose may result in a circulating level of 80 μmol, which will be adjusted down to about 40 μmol. In certain embodiments of any of the foregoing, subjects less than 15 years of age (e.g., less than 14, 13, 12, 11, 10, 9, 8, 7, 6, 5, 4, 3, 2 or 1 years of age) and having a body mass index (BMI) above the 97$^{th}$ percentile for their age are treated. In some embodiments, the subject has a BMI above 97$^{th}$ percentile for the age and weighs less than 65 kg. In some embodiment, these same subjects have high triglyceride levels, low LDH, and low or low normal adiponectin levels. In still another embodiment, the subjects have high or high normal resistin levels. In various embodiments of any of the foregoing, the patient weighs less than 65 kg. In various embodiments, the patient weighs from about 35-65 kg, or from about 40-60 kg, or from about 45-55 kg, or about 35, 40, 45, 50, 55, 60 or 65 kg. In various embodiments, the patient weighing less than 65 kg receives 600 to 1200 mg/day of cysteamine or cystamine composition or an amount to obtain circulating plasma levels of cysteamine of about 10-80 μmol (typically about 30-50 and more commonly about 40 μmol). In any of the foregoing embodiments, the subject has Type I NASH or NASH with Type 1 histological pattern. In still another embodiment of the foregoing the subject has lobular inflammation of the liver. In still another of further embodiment of any of the foregoing, the subject has low adiponectin and high triglycerides characteristic of NASH. In still another embodiment of any of the foregoing, the subject has a maker (e.g., AST, ALT, GGT or other liver marker having a level consistent with NASH as described herein.

In various embodiments, the patient weighs 65-80 kg, and may receive 750 to about 1500 mg/day of cysteamine or cystamine composition or an amount to obtain circulating plasma levels of cysteamine of about 10-80 μmol (typically about 30-50 and more commonly about 40 μmol). In any of the foregoing embodiments, the subject has Type I NASH. In still another embodiment of the foregoing the subject has lobular inflammation of the liver. In still another of further embodiment of any of the foregoing, the subject has low adiponectin and high triglycerides characteristic of NASH.

In various embodiments, the patient weighs more than 65 kg and receives 900 to about 2000 mg/day cysteamine or cystamine composition or an amount to obtain circulating plasma levels of cysteamine of about 10-80 μmol (typically about 30-50 and more commonly about 40 μmol). In any of the foregoing embodiments, the subject has Type I NASH. In still another embodiment of the foregoing the subject has lobular inflammation of the liver. In still another of further embodiment of any of the foregoing, the subject has low adiponectin and high triglycerides characteristic of NASH.

The subject can be an adult, adolescent or child. In various embodiments, the patient is from 2 to 7 years old, from 8 to 11 years old, from 9 to 12 years old, or from 13 to 18 years old. In various embodiments, an adolescent is from 10 to 19 years old as described in the National Institutes of Health standards.

In various embodiments, the administration results in a decrease in NAFLD Activity Score of two or more points, no worsening or improvement of fibrosis, reduction in serum aminotransferases and gammaglutamyl transpeptidase (GGT); reduction in MRI-determined hepatic fat fraction; changes to markers of oxidation and anti-oxidant status; changes in fasting insulin and glucose; an increase in circulating adiponectin levels; a decrease in circulating resistin levels; a decrease in triglyceride levels; a decrease in oxidized phospholipids; changes in weight, height, body mass index (BMI) and waist circumference; changes in the Pediatric Quality of Life score; changes to any symptoms that patient may have experienced; proportion with a change from a histological diagnosis of definite NASH or indeterminate for NASH to not NASH at end of treatment; individual histological characteristics at end of treatment compared to baseline such as steatosis (fatty liver), lobular inflammation, portal chronic inflammation, ballooning, fibrosis score and stage 1a versus 1b fibrosis; and, change in mean NAS.

In yet another embodiment, the cysteamine or cystamine composition is administered at a frequency of 4 or less times per day (e.g., one, two or three times per day). In various embodiments, the composition is a delayed or controlled release dosage form that provides increased delivery of the cysteamine or cysteamine derivative or cystamine or cystamine derivative to the small intestine.

The delay or controlled release form can provide a $C_{max}$ of the cysteamine or cystamine or derivatives thereof, or a biologically active metabolite thereof, that is at least about 35%, 50%, 75% or higher than the $C_{max}$ provided by an immediate release dosage form containing the same amount of the cysteamine or cystamine or derivatives thereof. In another embodiment, the delay and extended release formulation provides an improved AUC compared to immediately release forms of cysteamine. For example, the AUC is increased compared to an immediate release formulation. In yet another embodiment, the delayed or controlled release dosage form comprises an enteric coating that releases the cysteamine or cystamine composition when the composition reaches the small intestine or a region of the gastrointestinal tract of a subject in which the pH is greater than about pH 4.5. In various embodiments, the pH is between 4.5 and 6.5. In one embodiment, the pH is about 5.5 to 6.5. In one embodiment the cysteamine or cystamine is delivered throughout the small intestine providing an extended release in the small intestine.

In various embodiments, the enterically coated cysteamine or cystamine composition is granulated and the granulation is compressed into a tablet or filled into a capsule. In certain embodiments, the granules are enterically coated prior to compressing into a tablet or capsule. Capsule materials may be either hard or soft, and are typically sealed, such as with gelatin bands or the like. Tablets and capsules for oral use will generally include one or more commonly used excipients as discussed herein.

In a further embodiment, the cysteamine or cystamine composition is formulated as a capsule. In one embodiment, the capsule comprises the cysteamine or cystamine composition and the capsule is then enterically coated. Capsule formulations are prepared using techniques known in the art.

A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

In various embodiments, exemplary cysteamine or cystamine product formulations contemplated for use in the present methods include those described in International Patent Applications PCT/US2007/002325, PCT/US2014/042607 and PCT/US2014/042616 (the disclosure of which are incorporated herein by reference).

For administration of the dosage form, i.e., the tablet or capsule comprising the enterically coated cysteamine or cystamine composition, a total weight in the range of approximately 50 mg to 1000 mg is used. In various embodiments, the tablet or capsule comprises 25, 50, 75, 100, 125, 150, 175, 200, 225, 250, 275, 300, 400 or 500 mg active ingredient, and multiple tablets or capsules are administered to reach the desired dosage. The dosage form is orally administered to a subject in need thereof.

In addition, various prodrugs can be "activated" by use of the enterically coated cysteamine or cystamine composition. Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of prodrugs use S—S bonds. Weak reducing agents, such as cysteamine, reduce these bonds and release the drug. Accordingly, the compositions of the disclosure are useful in combination with pro-drugs for timed release of the drug. In this aspect, a pro-drug can be administered followed by administration of an enterically coated cysteamine or cystamine composition of the disclosure (at a desired time) to activate the pro-drug.

Prodrugs of cysteamine have been described previously. See, e.g., Andersen et al., In vitro Evaluation of Novel Cysteamine Prodrugs Targeted to g-Glutamyl Transpeptidase (poster presentation), which describes S-pivaloyl cysteamine derivatives, S-benzoyl cysteamine derivatives, S-acetyl cysteamine derivatives and S-benzoyl cysteamine) glutamate-ethyl ester). Omran et al., Bioorg Med Chem Lett., 21(8):2502-4, 2011, describes a folate pro-drug of cystamine as a treatment for nephropathic cystinosis.

In one embodiment, a cysteamine or cystamine composition of the disclosure provides a delayed and extended release composition comprising cysteamine (e.g., cystamine-HCl or cysteamine bitartrate or other salts of cysteamine) or cystamine (or salt thereof). In one embodiment, the composition comprises a core of cysteamine or salt thereof or cystamine of salt thereof and one or more pharmaceutical excipients or binder encapsulated in an enteric coating material. In one embodiment, the delayed and extended release composition comprises a core tablet of cysteamine or cystamine and a binder. In one embodiment, the cysteamine base of the tablet is about 50 mg and encapsulated in an enteric coating material having a thickness of about 60-100 μm (e.g., about 71, 73, 75, 77, or 79 μm or any value there between) and/or about 10-13% (e.g., about 10.5, 11.0, 11.2, 11.4, 11.6, 11.8, 12.0, 12.2, 12.4, 12.6, 12.8% of any value there between) by weight of the tablet. In another embodiment, the cysteamine base of the tablet is about 150 mg and encapsulated in an enteric coating material having a thickness of about 90-130 μm (e.g., about 97, 99, 101, 103, 105, 107, 109, 111, 113 μm or any value there between) and/or about 9-14% (e.g., about 9.5, 9.7, 9.9, 10.1, 10.3 10.5, 11.0, 11.2, 11.4, 11.6, 11.8, 12.0, 12.2, 12.4, 12.6, 12.8, 13.0, 13.2, 13.4, 13.6, 13.8% or any value there between) by weight of the tablet by weight of the tablet.

In any of the foregoing embodiments, the enteric coating material can be selected from the group comprising polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters. The composition can be administered orally or parenterally. In another embodiment, the method results in improvement in liver fibrosis compared to levels before administration of the cysteamine composition. In yet another embodiment, the method results in a reduction in fat content of liver, a reduction in the incidence of or progression of cirrhosis, or a reduction in the incidence of hepatocellular carcinoma. In one embodiment, the method results in a decrease in hepatic aminotransferase levels compared to levels before administration of the cysteamine composition. In a further embodiment, the administering results in a reduction in hepatic transaminase of between approximately 10% to 70%, e.g. 10, 20, 30, 40, 50, 60 or 70% or any value between these numbers, compared to levels before treatment. In yet another embodiment, the administering results in a reduction in alanine or aspartate aminotransferase levels in a treated patient to approximately 50%, 40%, 30%, 20% or 10% above normal ALT levels, or at normal ALT levels. In yet other embodiment, the administering results in a reduction in serum ferritin levels compared to levels before treatment with the cysteamine composition. In various embodiments, the administration results in a lowering of NAS score.

The methods and composition of the disclosure can also include administering a second agent in combination with a cysteamine or cystamine composition to treat fatty liver disease. Thus, in another embodiment of any of the foregoing methods or composition, the subject can be treated with a combination of active agents for treating NASH. The combination includes cysteamine or cystamine composition and one or more of metformin, statins, anti-oxidants, and/or antibodies against oxidized phospholipids. Such a combination has unexpected synergy due to a multifaceted approach to modulating inflammation and inflammatory mediators. Such a combination would increase the antioxidant effects of adiponectin by increasing adiponectin levels, reduce triglyceride levels thereby reducing circulating phospholipids, reduce insulin resistance, and block the proinflammatory effects of oxidized phospholipids.

The methods and compositions of the disclosure also include use of a cysteamine or cystamine composition in preparation of a medicament for treatment of fatty liver disease, and use of a cysteamine or cystamine composition in preparation of a medicament for administration in combination with a second agent for treating fatty liver disease. Also included are use of a second agent for treating fatty liver disease in preparation of a medicament for administration in combination with a cysteamine or cystamine composition. Further provided are kits comprising a cysteamine or cystamine composition for treatment of fatty liver disease, optionally with a second agent for treating fatty liver disease, and instructions for use in treatment of fatty liver disease. The term "fatty liver disease" may include or exclude NASH.

In various embodiments, the cysteamine composition is cysteamine or a pharmaceutically acceptable salt thereof. Exemplary salts include hydrochloride salt and bitartrate salts.

In various embodiments of the disclosure, the cysteamine or cystamine composition, is administered at a daily dose ranging from about 10 mg/kg to about 2.5 g/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values. In some embodiments, the cysteamine or cystamine composition is administered at a total daily dose of from approximately 0.25 $g/m^2$ to 4.0 $g/m^2$ body surface area, about 0.5-2.0 $g/m^2$ body surface area, or 1-1.5 $g/m^2$ body surface area, or 1-1.95 $g/m^2$ body surface area, or 0.5-1 $g/m^2$ body surface area, or about 0.7-0.8 $g/m^2$ body surface area, or about 1.35 $g/m^2$ body surface area, or about 1.3 to about 1.95 grams/$m^2$/day, or about 0.5 to about 1.5 grams/$m^2$/day, or about 0.5 to about 1.0 grams/$m^2$/day, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 $g/m^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 $g/m^2$ or may range between any two of the foregoing values.

In some embodiments, the delayed and extended release formulation comprises an enteric coating that releases the cysteamine or cystamine when the formulation reaches the small intestine or a region of the gastrointestinal tract of a subject in which the pH is greater than about pH 4.5. In various embodiments, the formulation releases at a pH of about 4.5 to 6.5, 4.5 to 5.5, 5.5 to 6.5 or about pH 4.5, 5.0, 5.5, 6.0 or 6.5.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

The disclosure provides cysteamine and cystamine compositions useful in the treatment of fatty liver diseases and disorders. A cysteamine or cystamine composition refers, generally, to cysteamine, cystamine, salts of either of the foregoing or a biologically active metabolite thereof, or combination of cysteamine or cystamine, and includes cysteamine or cystamine salts, esters, amides, alkylated compounds, prodrugs, analogs, phosphorylated compounds, sulfated compounds, or other chemically modified forms thereof, by such techniques as labeling (e.g., with radionuclides or various enzymes), or covalent polymer attachment such as pegylation (derivatization with polyethylene glycol).

A cysteamine or cystamine composition includes cysteamine, cystamine, biologically active metabolites, chemically modified forms of the compound, by such techniques as esterification, alkylation (e.g., C1, C2 or C3), labeling (e.g., with radionuclides or various enzymes), covalent polymer attachment such as pegylation (derivatization with polyethylene glycol) or any mixtures thereof. In some embodiments, cysteamine or cystamine compositions include, but are not limited to, hydrochloride salts, bitartrate salts, phosphorylated derivatives, and sulfated derivatives. Examples of other cysteamine or cystamine compositions include 2-aminopropane thiol-1, 1-aminopropane thiol-2, N- and S-substituted cysteamine, AET, aminoalkyl derivatives, phosphorothioate, amifostine (U.S. Pat. No. 4,816,482). In one embodiment, a cysteamine or cystamine composition specifically excludes N-acetylcysteine. In one embodiment, cysteamine or cystamine compositions comprise, but are not limited to, structures described below:

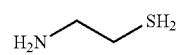

(I)

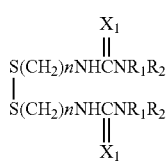

(II)

wherein n represents 2 or 3, $R_1$ and $R_2$ each represents a hydrogen atom, or an alkyl group optionally substituted by a hydroxy, amino, alkylamino or dialkylamino group, or represents a cycloalkyl or aryl group, and $X_1$ represents a group selected from the group consisting of =N—CN, =N—NO$_2$, =N—COR$_3$, =N—NR—COOR$_3$, =N—NR—CONH$_2$, =N—SO$_2$R$_3$, =CH—NO$_2$, —CH—SO$_2$R$_3$, =C(CN)$_2$, =C(CN)COOR$_3$ and =C(CN)CONH$_2$, wherein $R_3$ is an alkyl or aryl group. In another aspect, a cysteamine or cystamine composition can comprise a cysteamine radical linked to any number of non-toxic groups as set forth below:

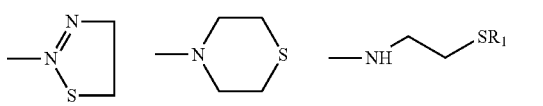

(III-V)

wherein $R_1$ represents hydrogen atom or a straight chain or a branched alkyl group having 1 to 10 carbon atoms.

Pharmaceutically acceptable salts of cysteamine or cystamine compositions are also included and comprise pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$^{4+}$) and substituted ammonium (N(R')$^{4+}$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

Cysteamine or cystamine compositions can be enterically coated. An enterically coated drug or tablet refers, generally, to a drug or tablet that is coated with a substance (an "enteric coating") that remains intact or substantially intact such that the drug or tablet is passed through the stomach but dissolves and releases the drug in the small intestine.

An enteric coating can be a polymer material or materials which encase a medicament core (e.g., cystamine, cysteamine, CYSTAGON® or other cysteamine product). PROCYSBI® is an example of an enteric formulation of cysteamine. Typically a substantial amount or all of the enteric coating material is dissolved before the medicament or therapeutically active agent is released from the dosage form, so as to achieve delayed dissolution or delivery of the medicament core. A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

The cysteamine or cystamine composition may also include additional pharmaceutically acceptable carriers or vehicles. A pharmaceutically acceptable carrier or vehicle refers, generally, to materials that are suitable for administration to a subject wherein the carrier or vehicle is not biologically harmful, or otherwise, cause undesirable effects. Such carriers or vehicles are typically inert ingredients of a medicament. Typically a carrier or vehicle is administered to a subject along with an active ingredient without causing any undesirable biological effects or interacting in a deleterious manner with any of the other components of a pharmaceutical composition in which it is contained.

A cysteamine or cystamine composition or other active ingredient can comprise a pharmaceutically acceptable salt, ester or other derivative. For example, salts, esters or other derivatives comprise biologically active forms having a similar biological effect compared to a parent compound. Exemplary salts include hydrochloride salt and bitartrate salts.

An active ingredient, pharmaceutical or other composition of the disclosure can comprise a stabilizing agent. Stabilizing agents, generally, refer to compounds that lower the rate at which a pharmaceutical degrades, particularly an oral pharmaceutical formulation under environmental conditions of storage.

As used herein, a "therapeutically effective amount" or "effective amount" refers to that amount of the compound sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In one embodiment, a therapeutically effective amount of the cysteamine or cystamine composition ameliorates symptoms, including but not limited to, liver fibrosis, fat content of liver, incidence of or progression of cirrhosis, incidence of hepatocellular carcinoma, increased hepatic aminotransferase levels, such as ALT and AST, increased serum ferritin, elevated levels of gamma-glutamyltransferase (gamma-GT), and elevated levels of plasma insulin, cholesterol and triglyceride.

The methods of compositions of the disclosure further provide enteric-coated compositions that result in less frequent dosing (2×/day vs. 4×/day), increased patient compliance and fewer gastrointestinal side effects (e.g., pain, heartburn, acid production, vomiting) and other side effects (e.g., patients smell like rotten eggs—a particular compliance problem as subjects reach puberty). The disclosure provides enteric-coated cysteamine compositions (sulfhydryl/CYSTAGON™) and cystamine compositions.

The disclosure provides methods for the treatment of fatty acid liver disease, including, but not limited to non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

The effectiveness of a method or composition of the described herein can be assessed, for example, by measuring leukocyte cystine concentrations. Additional measures of the efficacy of the methods of the disclosure include assessing relief of symptoms associated with fatty liver disease including, but not limited to, liver fibrosis, fat content of liver, incidence of or progression of cirrhosis, incidence of hepatocellular carcinoma, elevated hepatic aminotransferase levels, increased alanine aminotransferase (ALT), increased aspartate aminotransferase (AST), and elevated serum ferritin. Dosage adjustment and therapy can be made by a medical specialist depending upon, for example, the severity of fatty liver disease and/or the concentration of cystine. For example, treatment of fatty liver disease may result in a reduction in hepatic transaminase of between approximately 10% to 40% compared to levels before treatment. In a related embodiment, treatment results in a reduction in alanine anminotransferase levels in a treated patient to approximately 30%, 20% or 10% above normal ALT levels, or at normal ALT levels (≥40 iu/L). In another embodiment, treatment with cysteamine or cystamine composition results in a reduction in aspartate anminotransferase levels in a patient to approximately 30%, 20% or 10% above normal AST levels or back to normal AST levels.

In one embodiment, the disclosure provides methods of treating NAFL using cysteamine or cystamine compositions through reducing the oxidative stress caused by reactive oxygen species (ROS) in steatohepatitis. Cysteamine can achieve this through its direct or indirect ability to enhance glutathione levels within the liver. Glutathione has a protective effect against oxidative damage but itself does not enter easily into cells, even when given in large amounts treatment. Precursors of glutathione do, however, enter into cells and include cysteine, N-acetylcyteine, s-adenosylmethionine (SAMe) and other sulphur-containing compounds such as cysteamine.

The compositions of the disclosure can be used in combination with a second agent or other therapies useful for treating NAFLD or NASH or other fatty acid liver disorders. For example, cysteamine or cystamine compositions may be administered with drugs such as glitazones/thiazolidinediones that combat insulin resistance, including mesylate (troglitazone (REZULIN®)), rosiglitazone (AVANDIA®), pioglitazone (ACTOS®), as well as other agents, including, but not limited to, metformin, Sulfonylureas, Alpha-glucosidase inhibitors, Meglitinides, vitamin E, tetrahydrolipstatin (XENICAL™), milk thistle protein (SILIPHOS®), and antivirals.

Other therapies which reduce side effects of cysteamine or cystamine compositions can be combined with the methods and compositions of the disclosure to treat diseases and disorders that are attributed or result from NAFLD or NASH. Urinary phosphorus loss, for example, entails rickets, and it may be necessary to give a phosphorus supplement. Carnitine is lost in the urine and blood levels are low. Carnitine allows fat to be used by the muscles to provide energy. Hormone supplementation is sometimes necessary. Sometimes the thyroid gland will not produce enough thyroid hormones. This is given as thyroxin (drops or tablets). Insulin treatment is sometimes necessary if diabetes appears, when the pancreas does not produce enough insulin. These treatments have become rarely necessary in children whom are treated with cysteamine or cystamine composition, since the treatment protects the thyroid and the pancreas. Some adolescent boys require a testosterone treatment if puberty is late. Growth hormone therapy may be indicated if growth is not sufficient despite a good hydro electrolytes balance. Accordingly, such therapies can be combined with the cysteamine or cystamine compositions and methods of the disclosure. Additional therapies including the use of omeprazole (PRILOSEC®) can reduce adverse symptoms affecting the digestive tract.

The disclosure provides cysteamine or cystamine compositions useful in the treatment of fatty liver diseases and disorders. To administer cysteamine or cystamine compositions of the disclosure to human or test animals, it is preferable to formulate the cysteamine or cystamine compositions in a composition comprising one or more pharmaceutically acceptable carriers. As set out above, pharmaceutically or pharmacologically acceptable carriers or vehicles refer to molecular entities and compositions that do not produce allergic, or other adverse reactions when administered using routes well-known in the art, as described below, or are approved by the U.S. Food and Drug Administration or a counterpart foreign regulatory authority as an acceptable additive to orally or parenterally administered pharmaceuticals. Pharmaceutically acceptable carriers include any and all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The cysteamine or cystamine compositions may be administered orally, parenterally, transocularly, intranasally, transdermally, transmucosally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, compositions for administration parenterally are sterile.

Pharmaceutical compositions of the disclosure containing a cysteamine or cystamine composition as an active ingredient may contain pharmaceutically acceptable carriers or additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the disclosure.

Formulation of the pharmaceutical composition will vary according to the route of administration selected (e.g., solution, emulsion). An appropriate composition comprising the cysteamine or cystamine composition to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some embodiments, the cysteamine or cystamine composition of this disclosure can be lyophilized for storage and reconstituted in a suitable carrier prior to use. Any suitable lyophilization and reconstitution techniques can be employed. It is appreciated by those skilled in the art that lyophilization and reconstitution can lead to varying degrees of activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

In one embodiment, the disclosure provides use of an enterically coated cysteamine or cystamine composition. Enteric coatings prolong release until the cysteamine or cystamine composition reaches the intestinal tract, typically the small intestine. Because of the enteric coatings, delivery to the small intestine is improved thereby improving uptake of the active ingredient while reducing gastric side effects.

In some embodiments, the coating material is selected such that the therapeutically active agent is released when the dosage form reaches the small intestine or a region in which the pH is greater than pH 4.5. The coating may be a pH-sensitive material, which remain intact in the lower pH environs of the stomach, but which disintegrate or dissolve at the pH commonly found in the small intestine of the patient. For example, the enteric coating material begins to dissolve in an aqueous solution at pH between about 4.5 to about 5.5. For example, pH-sensitive materials will not undergo significant dissolution until the dosage from has emptied from the stomach. The pH of the small intestine gradually increases from about 4.5 to about 6.5 in the duodenal bulb to about 7.2 in the distal portions of the small intestine. In order to provide predictable dissolution corresponding to the small intestine transit time of about 3 hours (e.g., 2-3 hours) and permit reproducible release therein, the coating should begin to dissolve at the pH range within the small intestine. Therefore, the amount of enteric polymer coating should be sufficient to substantially dissolved during the approximate three hour transit time within the small intestine, such as the proximal and mid-intestine.

Enteric coatings have been used for many years to arrest the release of the drug from orally ingestible dosage forms. Depending upon the composition and/or thickness, the enteric coatings are resistant to stomach acid for required periods of time before they begin to disintegrate and permit release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See, Remington's at page 1590, and Zeitova et al. (U.S. Pat. No. 4,432,966), for descriptions of suitable enteric coating compositions. Accordingly, increased adsorption in the small intestine due to enteric coatings of cysteamine or cystamine composition compositions can result in improved efficacy.

Generally, the enteric coating comprises a polymeric material that prevents cysteamine or cystamine product release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a pKa in the range of about 3 to 5. Suitable enteric coating materials include, but are not limited to, polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit NE, Eudragit RL, Eudragit RS). For example, the enterically coating can comprise Eudragit L30D, triethylcitrate, and hydroxypropylmethylcellulose (HPMC), wherein the coating comprises 10 to 13% of the final product.

In one embodiment, the cysteamine or cystamine product composition is administered in tablet form. Tablets are manufactured by first enterically coating the cysteamine or cystamine product. A method for forming tablets herein is by direct compression of the powders containing the enterically coated cysteamine or cystamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In various embodiments, the enterically coated cysteamine or cystamine product is granulated and the granulation is compressed into a tablet or filled into a capsule. In certain embodiments, the granules are enterically coated prior to compressing into a tablet or capsule. Capsule materials may be either hard or soft, and are typically sealed, such as with gelatin bands or the like. Tablets and capsules for oral use will generally include one or more commonly used excipients as discussed herein.

In a further embodiment, the cysteamine or cystamine product is formulated as a capsule. In one embodiment, the capsule comprises the cysteamine or cystamine product and the capsule is then enterically coated. Capsule formulations are prepared using techniques known in the art.

A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

In various embodiments, exemplary cysteamine or cystamine product formulations contemplated for use in the present methods are described in International Patent Applications PCT/US14/42607 and PCT/US14/42616.

For administration of the dosage form, i.e., the tablet or capsule comprising the enterically coated cysteamine or cystamine product, a total weight in the range of approximately 100 mg to 1000 mg is used. In various embodiments, the tablet or capsule comprises 25, 50, 75, 100, 125, 150, 175, 200, 225, 250, 275, 300, 400 or 500 mg active ingredient, and multiple tablets or capsules are administered to reach the desired dosage. The dosage form is orally administered to a subject need thereof.

In some embodiments, the cysteamine or cystamine product composition is a delayed or controlled release dosage form that provides a $C_{max}$ of the cysteamine or cystamine product that is at least about 35%, 40%, 45%, 50%, 55%, 60%, 65%, 70%, 75%, 80%, 85%, or 100% higher than the $C_{max}$ provided by an immediate release dosage form containing the same amount of the cysteamine cystamine product. In some embodiments, the $C_{max}$ is up to about 75%, 100%, 125% or 150% higher than the $C_{max}$ of the immediate release dosage form. $C_{max}$ refers to the maximum dose of the cysteamine or cystamine product in the blood after dosing and provides an indicator that the drug is absorbed systemically.

In some embodiments, the AUC of the delayed or controlled release dosage form is also increased by at least about 20%, 25%, 30%, 35%, 40%, 45%, or 50%, or up to about 50%, 60%, 75% or 100% relative to an immediate release dosage form. AUC or "area under the curve", and refers to the kinetic curve derived when plasma drug concentration versus time is measured after dosing of a drug.

The preparation of delayed, controlled or sustained/extended release forms of pharmaceutical compositions with the desired pharmacokinetic characteristics is known in the art and can be accomplished by a variety of methods. For example, oral controlled delivery systems include dissolution-controlled release (e.g., encapsulation dissolution control or matrix dissolution control), diffusion-controlled release (reservoir devices or matrix devices), ion exchange resins, osmotic controlled release or gastroretentive systems. Dissolution controlled release can be obtained, e.g., by slowing the dissolution rate of a drug in the gastrointestinal tract, incorporating the drug in an in soluble polymer, and coating drug particles or granules with polymeric materials of varying thickness. Diffusion controlled release can be obtained, e.g., by controlling diffusion through a polymeric membrane or a polymeric matrix. Osmotically controlled release can be obtained, e.g., by controlling solvent influx across a semipermeable membrane, which in turn carries the drug outside through a laser-drilled orifice. The osmotic and hydrostatic pressure differences on either side of the membrane govern fluid transport. Prolonged gastric retention may be achieved by, e.g., altering density of the formulations, bioadhesion to the stomach lining, or increasing floating time in the stomach. For further detail, see the Handbook of Pharmaceutical Controlled Release Technology, Wise, ed., Marcel Dekker, Inc., New York, N.Y. (2000), incorporated by reference herein in its entirety, e.g. Chapter 22 ("An Overview of Controlled Release Systems").

The concentration of cysteamine or cystamine composition in these formulations can vary widely, for example from less than about 0.5%, usually at or at least about 1% to as much as 15 or 20% by weight and are selected primarily based on fluid volumes, manufacturing characteristics, viscosities, etc., in accordance with the particular mode of administration selected. Actual methods for preparing administrable compositions are known or apparent to those skilled in the art and are described in more detail in, for example, Remington's Pharmaceutical Science, 15th ed., Mack Publishing Company, Easton, Pa. (1980).

The cysteamine or cystamine composition is present in the composition in a therapeutically effective amount; typically, the composition is in unit dosage form. The amount of cysteamine or cystamine composition administered will, of course, be dependent on the age, weight, and general condition of the subject, the severity of the condition being treated, and the judgment of the prescribing-physician. Suitable therapeutic amounts will be known to those skilled in the art and/or are described in the pertinent reference texts and literature. Current non-enterically coated doses are about 1.35 g/m² body surface area and are administered 4-5 times per day. In one aspect, the dose is administered either one time per day or multiple times per day. The cysteamine or cystamine composition may be administered one, two or three or four times per day.

In some embodiments, the cysteamine or cystamine composition may be administered at a total daily dose of about 1-1.5 g/m² body surface area, or 0.5-1 g/m² body surface area, or about 0.7-0.8 g/m² body surface area, or about 1.35 g/m² body surface area. Salts or esters of the same active ingredient may vary in molecular weight depending on the type and weight of the salt or ester moiety. For administration of the dosage form, e.g., a tablet or capsule or other oral dosage form comprising the enterically coated cysteamine or cystamine composition, a total weight in the range of approximately 100 mg to 1000 mg is used. The dosage form is orally administered to a patient suffering from fatty liver disease for which a cysteamine or cystamine composition would be indicated, including, but not limited to, NAFLD and NASH. Administration may continue for at least 3 months, 6 months, 9 months, 1 year, 2 years, or more.

Compositions useful for administration may be formulated with uptake or absorption enhancers to increase their efficacy. Such enhancer include for example, salicylate, glycocholate/linoleate, glycholate, aprotinin, bacitracin, SDS, caprate and the like. See, e.g., Fix (J. Pharm. Sci., 85:1282-1285, 1996) and Oliyai and Stella (Ann. Rev. Pharmacol. Toxicol., 32:521-544, 1993).

The enterically coated cysteamine or cystamine composition can comprise various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the cysteamine or cystamine composition. For solid compositions, diluents are typically necessary to increase the bulk of a tablet so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a tablet formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum. Lubricants are used to facilitate tablet manufacture; examples of suitable lubricants include, for example, magnesium stearate, calcium stearate, and stearic acid, and are typically present at no more than approximately 1 weight percent relative to tablet weight. Disintegrants are used to facilitate tablet disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

A pharmaceutical composition may also comprise a stabilizing agent such as hydroxypropyl methylcellulose or polyvinylpyrrolidone, as disclosed in U.S. Pat. No. 4,301,146. Other stabilizing agents include, but are not limited to, cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of cysteamine or cystamine composition to the stabilizing agent is at least about 1:500 w/w, more commonly about 1:99 w/w.

In an alternative embodiment, the enterically coated cysteamine or cystamine composition are granulated and the granulation is compressed into a tablet or filled into a capsule. Capsule materials may be either hard or soft, and are typically sealed, such as with gelatin bands or the like. Tablets and capsules for oral use will generally include one or more commonly used excipients as discussed herein.

For administration of the dosage form, i.e., the tablet or capsule comprising the enterically coated cysteamine or cystamine composition, a total weight in the range of approximately 100 mg to 1000 mg is used. The dosage form is orally administered to a patient suffering from a condition for which a cysteamine or cystamine composition would typically be indicated, including, but not limited to, NAFLD and NASH.

The compositions of the disclosure can be used in combination with other therapies useful for treating NAFL and NASH. For example, antioxidants such as glycyrrhizin, schisandra extract, ascorbic acid, glutathione, silymarin, lipoic acid, and d-alpha-tocopherol, and parenterally administering to the subject glycyrrhizin, ascorbic acid, glutathione, and vitamin B-complex may be administered in combination (either simultaneously in a single composition or in separate compositions). Alternatively, the combination of therapeutics can be administered sequentially.

The effectiveness of a method or composition of the disclosure can be assessed by measuring fatty acid content and metabolism in the liver. Dosage adjustment and therapy can be made by a medical specialist depending upon, for example, the severity of NAFL.

It is to be understood that while the disclosure has been described in conjunction with specific embodiments thereof, that the foregoing description as well as the examples which follow are intended to illustrate and not limit the scope of the disclosure. Other aspects, advantages and modifications within the scope of the disclosure will be apparent to those skilled in the art to which the disclosure.

EXAMPLES

A study of Cysteamine Bitartrate Delayed-Release for the Treatment of Nonalcoholic Fatty Liver Disease (NAFLD) in Children (CyNCh) was conducted in conjunction with the National Institute of Diabetes and Digestive and Kidney Diseases (NIDDK). CyNCh was a multi-center, randomized, placebo-controlled clinical trial of 169 children ages eight to 17 years with biopsy-confirmed moderate-to-severe NAFLD. Patients were randomized to receive placebo or a specified fixed dose of RP103 (enterically coated granulated cysteamine bitartrate; Raptor Pharmaceuticals, Inc.) based on weight: 600 mg/day (≤65 kg), 750 mg/day (65-80 kg) or 900 mg/day (≥80 kg) for 52 weeks. The primary objective was to evaluate whether 52 weeks of treatment with RP103 would result in improvement in liver disease severity defined as: (1) a decrease in NAFLD Activity Score of two or more points, and; (2) no worsening of fibrosis. Secondary end-points included: reduction in serum aminotransferase and gammaglutamyl transpeptidase (GGT); reduction in MRI-determined hepatic fat fraction; changes to markers of oxidation and anti-oxidant status; changes in fasting insulin and glucose; changes in weight, height, body mass index (BMI) and waist circumference; changes in the Pediatric Quality of Life score; changes to any symptoms that patient may have experienced; proportion with a change from a histological diagnosis of definite NASH or indeterminate for NASH to not NASH at end of treatment; individual histological characteristics at end of treatment compared to baseline such as steatosis (fatty liver), lobular inflammation, portal chronic inflammation, ballooning, fibrosis score and stage 1a versus 1b fibrosis; and, change in mean NAS. End of study biopsies were conducted in patients after the 52-week treatment period, with all biopsies centrally scored in a blinded fashion. Subjects not completing 52 weeks of treatment or subjects completing 52 weeks of treatment but refusing a biopsy were consider non-responders for the purpose of the primary analyses.

An evaluation of the primary endpoint of change in baseline liver histology as measured by a NAS score decrease of ≥2 and no worsening of fibrosis, there was no difference in the response rate between RP103 and placebo (28% versus 22%, respectively; p=0.34). Based upon additional analyses of the CyNCh study conducted by NIDDK researchers, RP103 demonstrated a significant effect on the NAFLD Activity Score, or NAS, in a post-hoc analysis of patients weighing less than or equal to 65 kg at enrollment.

Initial analysis shows that no statistically significant difference was seen in the components of the NAS score or fibrosis; however an improvement in the number of subjects with lobular inflammation was observed (36% and 21% in RP103 and placebo groups, respectively; p=0.03), though not statistically significant when adjusted for multiple comparisons.

A post-hoc analysis evaluating response by baseline weight category of ≤65 kg versus >65 kg demonstrated a statistically significant difference in the primary endpoint of improvement in liver histology in the lower weight category, favoring RP103 versus placebo (p=0.01). This cohort represented approximately 28% of the population of subjects enrolled and received the lowest assigned dose of 600 mg per day. An improvement in liver histology was not observed in subjects >65 kg.

A statistically significant improvement in liver transaminases, ALT and AST (p=0.02 and p=0.008, respectively), and GGT (p=0.02) between RP103 and placebo was seen as measured by the mean change from baseline after 52 weeks of treatment. There were no differences in adverse events observed in children on RP103 compared to placebo.

Tables 1, 2 and 3 demonstrate liver function and effects on control and treated subjects with RP103.

TABLE 1

Baseline characteristics of the study population

|  | Cysteamine bitartrate (N = 88) | Placebo (N = 81) | Total (N = 169) |
| --- | --- | --- | --- |
| Weight stratum | | | |
| <65 kg | 24 (27%) | 23 (28%) | 47 (28%) |
| 65-80 kg | 14 (16%) | 10 (12%) | 24 (14%) |
| >80 kg | 50 (57%) | 48 (59%) | 98 (58%) |
| Demographics | | | |
| Age (years) | 13.8 (2.9) | 13.6 (2.5) | 13.7 (2.7) |
| Male | 63 (72%) | 56 (69%) | 119 (70%) |
| Race | | | |
| American Indian/Alaska Native | 5 (6%) | 6 (7%) | 11 (7%) |
| Asian | 0 (0%) | 2 (2%) | 2 (1%) |
| Black or African-American | 3 (3%) | 3 (4%) | 6 (4%) |
| White | 56 (64%) | 46 (57%) | 102 (60%) |
| More than one race | 3 (3%) | 1 (1%) | 4 (2%) |
| Refusal/not stated | 21 (24%) | 23 (28%) | 44 (26%) |
| Hispanic ethnicity | 66 (75%) | 58 (72%) | 124 (73%) |
| Self-Reported Pediatric QOL* | | | |
| Physical health | 61 (15) | 82 (19) | 61 (17) |
| Psychosocial health | 75 (16) | 77 (16) | 76 (16) |
| Parent/guardian-Reported Pediatric QOL* | | | |
| Physical health | 68 (21) | 69 (24) | 68 (23) |
| Psychosocial health | 67 (19) | 68 (18) | 68 (19) |
| Liver enzymes | | | |
| Alanine aminotransferase (U/L) - median (IQR) | 93 (67-175) | 80 (61-120) | 87 (62-151) |
| Aspartate aminotransferase (U/L) - median (IQR) | 55 (40-91) | 49 (38-69) | 52 (39-79) |
| Alkaline phosphatase (U/L) | 224 (116) | 214 (101) | 220 (109) |
| γ-glutamyl transpeptidase (U/L) | 50 (33) | 44 (29) | 47 (31) |
| Total bilirubin (mg/dL) | 0.54 (0.34) | 0.50 (0.26) | 0.52 (0.30) |
| Lipids | | | |
| Total cholesterol (mg/dL) | 165 (40) | 163 (37) | 164 (38) |
| HDL cholesterol (mg/dL) | 39 (9) | 41 (9) | 40 (9) |

TABLE 1-continued

Baseline characteristics of the study population

| | Cysteamine bitartrate (N = 88) | Placebo (N = 81) | Total (N = 169) |
|---|---|---|---|
| LDL cholesterol (mg/dL) | 95 (32) | 92 (31) | 94 (31) |
| Non-HDL cholesterol (mg/dL) | 126 (40) | 122 (37) | 124 (39) |
| Triglycerides (mg/dL) | 160 (81) | 157 (77) | 158 (79) |
| Hematology | | | |
| Hemoglobin (g/dL) | 14 (1) | 14 (1) | 14 (1) |
| Hematocrit (%) | 41 (4) | 41 (3) | 41 (4) |
| Mean corpuscular volume (fL) | 84 (4) | 84 (4) | 84 (4) |
| White blood cell count (×10$^9$ per L) | 7.9 (2.2) | 7.7 (1.8) | 7.8 (2.0) |
| Platelet count (×10$^9$ per L) | 287 (57) | 291 (69) | 289 (63) |
| Chemistries | | | |
| Bicarbonate (mEg/L) | 25.0 (2.3) | 24.8 (2.4) | 24.9 (2.3) |
| Calcium (mg/dL) | 9.7 (0.4) | 9.8 (0.5) | 9.7 (0.4) |
| Creatinine (mg/dL) | 0.6 (0.1) | 0.6 (0.2) | 0.6 (0.2) |
| Chemstries | | | |
| Uric acid (mg/dL) | 6.1 (1.6) | 5.8 (1.5) | 5.9 (1.5) |
| Albumin (g/dL) | 4.6 (0.3) | 4.5 (0.4) | 4.6 (0.3) |
| Total protein (g/dL) | 7.7 (0.4) | 7.7 (0.5) | 7.7 (0.4) |
| Other laboratory results | | | |
| Prothrombin times (s) | 11.8 (1.4) | 12.0 (1.4) | 11.9 (1.4) |
| International normalized ratio | 1.02 (0.07) | 1.03 (0.06) | 1.02 (0.07) |
| Metabolic factors | | | |
| Fasting serum glucose (mg/dL) | 87 (10) | 88 (14) | 88 (12) |
| Insulin (μU/mL)[†] | 35 (31) | 38 (34) | 36 (32) |
| HOMA-IR[‡] (glucose [mmol/L] × insulin [μU/mL]/22.5) | 7.7 (7.5) | 8.4 (7.7) | 8.0 (7.6) |
| Weight (kg) | 85 (26) | 84 (25) | 85 (25) |
| Body-mass index (kg/m$^2$) | 33 (7) | 32 (6) | 32 (6) |
| Body-mass index z-score | 2.2 (0.5) | 2.2 (0.4) | 2.2 (0.4) |
| Waist circumference (cm) | 104 (15) | 103 (15) | 103 (15) |
| Waist-to-hip ratio | 0.97 (0.07) | 0.98 (0.07) | 0.98 (0.07) |
| Systolic blood pressure (mm Hg) | 120 (11) | 120 (12) | 120 (11) |
| Diastolic blood pressure (mm Hg) | 68 (8) | 67 (10) | 67 (9) |
| Comorbidities | | | |
| Diabetes | 1 (1%) | 7 (9%) | 8 (5%) |
| Hypertension | 9 (10%) | 6 (7%) | 15 (9%) |
| Hyperlipidemia | 13 (15%) | 12 (15%) | 25 (15%) |
| Medications in the past 6 months | | | |
| Metformin | 10 (11%) | 9 (11%) | 19 (11%) |
| Vitamin E | 3 (3%) | 1 (1%) | 4 (2%) |
| Cardiovascular/antihypertensive | 8 (9%) | 7 (9%) | 15 (9%) |
| Antilipidemic | 0 (0%) | 3 (4%) | 3 (2%) |
| Liver histology findings | | | |
| Steatohepetitis | | | |
| No | 25 (28%) | 19 (23%) | 44 (26%) |
| Borderline Zone 3 pattern | 16 (18%) | 10 (12%) | 26 (15%) |
| Borderline Zone 1, periportal pattern | 23 (26%) | 29 (36%) | 52 (31%) |
| Definite | 24 (27%) | 23 (28%) | 47 (28%) |
| Fibrosis stage | | | |
| None | 24 (27%) | 25 (31%) | 49 (29%) |
| Mild, zone 3 perisinusoidal | 9 (10%) | 7 (9%) | 16 (9%) |
| Moderate, zone 3 perisinusoidal | 6 (7%) | 5 (6%) | 11 (7%) |
| Portal/periportal only | 20 (23%) | 20 (25%) | 40 (24%) |
| Zone 3 and periportal, any combination | 9 (10%) | 13 (16%) | 22 (13%) |
| Bridging | 19 (22%) | 11 (14%) | 30 (18%) |
| Cirrhosis | 1 (1%) | 0 (0%) | 1 (1%) |
| Fibrosis stage[§] | 1.3 (1.1) | 1.1 (1.0) | 1.2 (1.1) |
| Steatosis score | 2.3 (0.8) | 2.5 (0.7) | 2.4 (0.7) |
| Lobular inflammation score | 1.8 (0.7) | 1.6 (0.7) | 1.7 (0.7) |
| Hepatocellular ballooning score | 0.6 (0.7) | 0.6 (0.8) | 0.6 (0.7) |
| Portal inflammation score[¶] | 1.1 (0.5) | 1.1 (0.5) | 1.1 (0.5) |
| NAFLD activity score[∥] | 4.7 (1.4) | 4.6 (1.4) | 4.7 (1.4) |

TABLE 2

Changes in histological features of the liver after 52 weeks of treatment
Changes in histological features of the liver after 52 weeks of treatment

|  | Cysteamine bitartrate | Placebo | Relative improvement ratio or mean changes from baseline* (95% CI) Cysteamine vs. placebo | P* |
|---|---|---|---|---|
| Historic Improvement - Primary Outcome† |  |  |  |  |
| Number of patients | 88 | 81 |  |  |
| Patients with improvement | 25 (28%) | 16 (22%) | 1.3 (0.8, 2.1) | 0.34 |
| Histologic Improvement - Completed follow-up |  |  |  |  |
| Number of patients | 71 | 75 |  |  |
| Patients with improvement | 25 (35%) | 18 (24%) | 1.4 (0.9, 2.4) | 0.16 |
| Histologic Improvement - Adherent/Not adherent‡ |  |  |  |  |
| Adherent to prescribed dose |  |  |  |  |
| Number of patients | 29 | 40 |  |  |
| Patients with improvement | 10 (34%) | 7 (18%) | 2.0 (0.8-5.0) | 0.12 |
| Not adherent to prescribed dose |  |  |  |  |
| Number of patients | 59 | 41 |  |  |
| Patients with improvement | 15 (25%) | 11 (27%) | 0.9 (0.5-1.9) | 0.87 |
| Changes from baseline in histological features§ |  |  |  |  |
| Resolution of indeterminate or definite nonalcoholic steatohepatitis¶ | 18 (29%) | 17 (27%) | 1.1 (0.6, 1.8) | 0.85 |
| Fibrosis ‖ |  |  |  |  |
| Patients with improvement | 25 (28%) | 23 (28%) | 1.0 (0.6, 1.6) | 0.98 |
| Change in score | −0.3 ± 0.9 | −0.1 ± 1.0 | −0.2 (−0.4, 0.1) | 0.24 |
| Total NAFLD activity score |  |  |  |  |
| Change in score | −0.8 ± 1.8 | −0.8 ± 1.8 | 0.0 (−0.6, 0.5) | 0.90 |
| Hepatocellular ballooning |  |  |  |  |
| Patients with improvement | 17 (19%) | 21 (26%) | 0.8 (0.4, 1.3) | 0.29 |
| Change in score | −0.1 ± 0.7 | −0.3 ± 0.8 | 0.1 (−0.1, 0.3) | 0.15 |
| Steatosis |  |  |  |  |
| Patients with improvement | 26 (30%) | 33 (41%) | 0.7 (0.5, 1.1) | 0.15 |
| Change in score | −0.3 ± 0.9 | −0.4 ± 0.9 | 0.1 (−0.2, 0.4) | 0.59 |
| Lobular inflammation |  |  |  |  |
| Patients with improvement | 32 (36%) | 17 (21%) | 1.8 (1.1, 2.9) | 0.03 |
| Change in score | −0.4 ± 0.8 | −0.1 ± 0.8 | −0.2 (−0.4, 0.0) | 0.06 |
| Portal inflammation** |  |  |  |  |
| Patients with improvement | 16 (20%) | 14 (17%) | 1.2 (0.6, 2.3) | 0.57 |
| Change in score | −0.1 ± 0.6 | −0.1 ± 0.6 | 0.0 (−0.2, 0.2) | 0.76 |

Data are n (%) or mean ± SD.

TABLE 3

Changes in liver enzymes, serum biochemical tests, metabolic factors, and quality of life from baseline to 52 weeks.
Changes in liver enzymes, serum biochemical tests, metabolic factors, and quality of life from baseline to 52 weeks

|  | Crude Change from baseline to 52 weeks (mean[SD]) | | Adjusted Mean changes from baseline (cysteamine bitartrate vs. placebo) (95% CI) | P |
|---|---|---|---|---|
|  | Cysteamine bitartrate (N = 75) | Placebo (N = 77) |  |  |
| Liver enzymes |  |  |  |  |
| Alanine aminotransferase (U/L) | −53 (88) | −8 (77) | −24 (−44, −4) | 0.02 |
| Aspartate aminotransferase (U/L) | −31 (52) | −4 (36) | −15 (−26, −4) | 0.008 |
| Alkaline phosphatase (U/L) | −31 (70) | −19 (54) | −9 (−28, 10) | 0.37 |
| γ-glutamyl transpeptidase (U/L) | −10 (23) | −1 (16) | −7 (−13, −1) | 0.02 |
| Total bilirubin (mg/dL) | 0.01 (0.34) | 0.01 (0.22) | 0.01 (−0.07, 0.10) | 0.80 |

TABLE 3-continued

Changes in liver enzymes, serum biochemical tests, metabolic factors, and quality of life from baseline to 52 weeks.
Changes in liver enzymes, serum biochemical tests, metabolic factors, and quality of life from baseline to 52 weeks

|  | Crude Change from baseline to 52 weeks (mean[SD]) | | Adjusted Mean changes from | |
| --- | --- | --- | --- | --- |
|  | Cysteamine bitartrate (N = 75) | Placebo (N = 77) | baseline (cysteamine bitartrate vs. placebo) (95% CI) | P |
| Normalization of ALT (≤30 U/L in males; ≤21 U/L in females) | 10 (14%) | 7 (9%) |  | 0.45 |
| Lipids |  |  |  |  |
| Total cholesterol (mg/dL) | −11 (23) | −4 (22) | −6 (−13, 0) | 0.07 |
| HDL cholesterol (mg/dL) | 0.0 (6.2) | −0.4 (7.6) | −0.6 (−2.7, 1.6) | 0.61 |
| LDL cholesterol (mg/dL) | −10 (19) | −3 (20) | −5 (−11, 1) | 0.09 |
| Non-HDL cholesterol (mg/dL) | −11 (22) | −4 (19) | −6 (−13, 0) | 0.06 |
| Triglycerides (mg/dL) | −7 (60) | 0 (68) | −5 (−25, 14) | 0.59 |
| Hematology |  |  |  |  |
| Hemoglobin (g/dL) | 0.2 (0.9) | 0.2 (0.8) | −0.1 (−0.3, 0.2) | 0.64 |
| Hematocrit (%) | 0.8 (2.5) | 0.7 (2.4) | 0.0 (−0.7, 0.8) | 0.90 |
| Mean corpuscular volume (fL) | 0.4 (2.2) | 0.0 (2.1) | 0.4 (−0.3, 1.0) | 0.31 |
| White blood cell count (×10$^9$ per L) | −0.4 (2.0) | −0.3 (1.8) | 0.0 (−0.6, 0.5) | 0.95 |
| Platelet count (×10$^9$ per L) | −10 (33) | −6 (37) | −5 (−16, 6) | 0.34 |
| Chemistries |  |  |  |  |
| Bicarbonate (mEg/L) | −0.6 (2.7) | 0.1 (2.6) | −0.4 (−1.2, 0.4) | 0.32 |
| Calcium (mg/dL) | −0.1 (0.5) | −0.1 (0.4) | 0.0 (−0.2, 0.1) | 0.49 |
| Creatinine (mg/dL) | 0.02 (0.10) | 0.03 (0.11) | 0.0 (0.0, 0.0) | 0.89 |
| Uric acid (mg/dL) | 0.0 (1.2) | 0.3 (1.1) | −0.2 (−0.5, 0.2) | 0.36 |
| Albumin (g/dL) | −0.1 (0.3) | −0.1 (0.3) | 0.0 (−0.1, 0.1) | 0.92 |
| Total protein (g/dL) | −0.1 (0.5) | −0.1 (0.5) | 0.0 (−0.2, 0.1) | 0.86 |
| Other laboratory results |  |  |  |  |
| Prothrombin time (s) | 0.0 (1.2) | −0.2 (1.2) | 0.2 (−0.2, 0.5) | 0.36 |
| International normalized ratio | 0.02 (0.09) | 0.02 (0.06) | 0.00 (−0.03, 0.02) | 0.76 |
| Metabolic factors |  |  |  |  |
| Fasting serum glucose (mg/dL) | 1 (12) | 5 (27) | −4 (−11, 3) | 0.24 |
| Insulin (μU/mL)† | 6 (36) | 10 (40) | −6 (−18, 6) | 0.34 |
| HOMA-IR (glucose [mmol/L] × insulin‡ [pmol/L]22.5) | 1.4 (9.2) | 3.6 (12.5) | −2.6 (−6.2, 1.0) | 0.15 |
| Weight (kg) | 6.3 (9.3) | 7.8 (6.6) | −1.5 (−4.1, 1.1) | 0.25 |
| Body-mass index (kg/m$^2$) | 0.8 (2.8) | 1.1 (2.2) | −0.3 (−1.1, 0.5) | 0.42 |
| Body-mass index z-score | −0.1 (0.3) | 0 (0.2) | −0.1 (−0.1, 0.0) | 0.11 |
| Waist circumference (cm) | 2.5 (7.7) | 2.3 (7.5) | 0.2 (−2.3, 2.6) | 0.89 |
| Waist-to-hip ratio | 0.00 (0.06) | −0.01 (0.06) | 0.00 (−0.01, 0.02) | 0.77 |
| Systolic blood pressure (mm Hg) | 3 (12) | 2 (12) | 1 (−3, 4) | 0.71 |
| Diastolic blood pressure (mm Hg) | −1 (9) | 1 (9) | −1 (−4, 1) | 0.31 |
| Self-Reported Pediatric QOL* |  |  |  |  |
| Physical health | 4 (17) | 5 (16) | −1 (−5, 3) | 0.77 |
| Psychosocial health | 4 (15) | 5 (14) | −1 (−5, 3) | 0.64 |
| Parent/guardian-Reported Pediatric QOL* |  |  |  |  |
| Physical health | 4 (27) | 5 (24) | −2 (−9, 5) | 0.58 |
| Psychosocial health | 5 (18) | 6 (24) | −1 (−6, 5) | 0.85 |

P-values and means changes from baseline were calculated using ANCOVA models, regressing change from baseline to 52 weeks on treatment group and baseline value of the outcome.
Number of patients in the cysteamine bitartrate group ranged from 70 to 75 and number of patients in the placebo group ranged from 73 to 77 due to missing values.

Numerous modifications and variations in the invention as set forth in the above illustrative examples are expected to occur to those skilled in the art. Consequently only such limitations as appear in the appended claims should be placed on the invention.

What is claimed:

1. A method of treating a subject comprising:
   measuring one or more markers of liver function in the blood, plasma or serum of the subject;
   measuring resistin, adiponectin and/or cytokeratin 18 levels in the blood, plasma or serum of the subject;
   determining if the subject's BMI is above the 97$^{th}$ percentile for the subject's age;
   determining if the subject has lobular inflammation or portal inflammation;
   identifying a subject with (i) liver function and resistin, adiponectin and/or cytokeratin 18 levels characteristic of a fatty liver disease, and (ii) lobular inflammation; and administering a therapeutically effective amount of a cysteamine salt or cystamine salt composition to the patient to obtain a plasma level of about 10-80 μmol of cysteamine in the plasma.

2. The method of claim 1, wherein the fatty liver disease is selected from the group consisting of non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

3. The method of claim 1, wherein the one or more markers of liver function are selected from the group consisting of alanine aminotransferase (ALT), alkaline phosphatase (ALP), aspartate aminotransferase (AST), gamma-glutamyl transpeptidase (GGT) and triglycerides.

4. The method of claim 3, wherein an ALT level of about 60-150 units/liter is indicative of fatty liver disease, wherein an ALP level of about 150-250 units/liter is indicative of fatty liver disease, wherein an AST level of about 40-100 units/liter is indicative of fatty liver disease, wherein a GGT level of 50-100 units/liter is indicative of fatty liver disease, wherein a triglyceride level above 150 mg/dL and/or high LDL level is indicative of fatty liver disease, and/or wherein a resistin level of greater than 8 ng/ml is indicative of fatty liver disease.

5. The method of claim 1, wherein an adiponectin level decreased by at least about 20% from age and sex matched normal subjects is indicative of fatty liver disease.

6. The method of claim 1, wherein the patient's BMI is above the 97$^{th}$ percentile for the patient's age and the patient weighs less than or equal to 65 kg.

7. The method of claim 1, wherein the patient comprises a BMI above 97$^{th}$ percentile for age and weighs less than 65 kg and has triglyceride levels associated with NASH.

8. The method of claim 1, wherein the cysteamine salt composition is an enterically coated composition.

9. The method of claim 8, wherein the cysteamine salt compositions comprise granules or tablets.

10. The method of claim 9, wherein the cysteamine salt composition comprises (i) a core particle comprising a mixture of cysteamine bitartrate and a binder, and (ii) an enteric membrane surrounding the core particle; wherein the beads have a distribution of particle sizes in a range of about 0.7 mm to about 2.8 mm; wherein the enteric membrane begins to dissolve within a pH range of about 4.5 to about 6.5; wherein the enteric membrane is present in an amount in a range of about 25% to about 35% by weight, based on the weight of the core particles; and wherein the pharmaceutical dosage form, upon administration in a capsule to fasted healthy normal subjects at 600 mg free cysteamine base, provides: (a) a mean $C_{max}$ upon oral dosing in a range of 2.3±0.6 mg/L or in a range of 80% to 125% thereof; (b) a mean AUC (0-∞) upon oral dosing in a range of 0.84±0.19 min*mg/L/mg or in a range of 80% to 125% thereof; and (c) a plasma cysteamine level of 10-80 μmol.

11. The method of claim 9, wherein the cysteamine salt composition comprises (i) a core tablet comprising a mixture of cysteamine bitartrate and a binder, and (ii) an enteric membrane surrounding the tablet, wherein the thickness of the enteric coating increases from 70 μm to 115 μm relative to the cysteamine base dose from 50 mg to 300 mg, and/or wherein the enteric coating is present in an amount in a range of about 9 to about 15% by weight of the core tablet and wherein upon delivery to a fasted healthy normal subject at 600 mg free cysteamine base the dose provides a plasma cysteamine level of 10-80 μm.

12. The method of claim 1, wherein the cystamine salt composition is an enterically coated composition.

13. The method of claim 12, wherein the cystamine salt compositions comprise granules or tablets.

14. The method of claim 12, wherein the cystamine salt composition comprises (i) a core particle comprising a mixture of cystamine and a binder, and (ii) an enteric membrane surrounding the core particle; wherein the beads have a distribution of particle sizes in a range of about 0.7 mm to about 2.8 mm; wherein the enteric membrane begins to dissolve within a pH range of about 4.5 to about 6.5; wherein the enteric membrane is present in an amount in a range of about 25% to about 35% by weight, based on the weight of the core particles; and wherein the pharmaceutical dosage form, upon administration in a capsule to fasted healthy normal subjects at 600 mg free cystamine base, provides: (a) a mean $C_{max}$ upon oral dosing in a range of 2.3±0.6 mg/L or in a range of 80% to 125% thereof; (b) a mean AUC (0-∞) upon oral dosing in a range of 0.84±0.19 min*mg/L/mg or in a range of 80% to 125% thereof; and (c) a plasma cysteamine level of 10-80 μmol.

15. The method of claim 9, wherein the cystamine salt composition comprises (i) a core tablet comprising a mixture of cystamine and a binder, and (ii) an enteric membrane surrounding the core tablet, wherein the thickness of the enteric coating increases from 60 μm to 130 μm relative to the cystamine dose from 50 mg to 300 mg, and/or wherein the enteric coating is present in an amount in a range of about 9 to about 15% by weight of the core tablet and wherein upon delivery to a fasted healthy normal subject at 600 mg cystamine the dose provides a plasma cysteamine level of 10-80 μm.

16. A method of treating a patient having Non-alcoholic steatohepatitis (NASH) and having lobular inflammation with little to no portal inflammation with a cysteamine or cystamine composition.

17. The method of claim 16, wherein the patient comprises a BMI that is greater than 97$^{th}$ percentile for the patient's age group.

18. The method of claim 17, wherein the patient is less than 65 kg.

19. The method of claim 16, wherein the total daily dose of cysteamine or cystamine composition is about 0.5-2.0 g/m$^2$.

20. The method of claim 16, wherein the composition is administered at a frequency of 4 or less times per day.

21. The method of claim 16, wherein the composition is a delayed and extended release dosage form that provides increased delivery of the cysteamine or cystamine composition to the small intestine.

22. The method of claim 21, wherein the delayed and extended release dosage form provides a $C_{max}$ of the cysteamine or cysteamine derivative, or a biologically active metabolite thereof, that is at least about 35% higher than the $C_{max}$ provided by an immediate release dosage form containing the same amount of the cysteamine or cysteamine derivative.

23. The method of claim 21, wherein the delayed and extended release dosage form comprises an enteric coating that releases the cysteamine or cystamine composition when the composition reaches the small intestine or a region of the gastrointestinal tract of a subject in which the pH is greater than about pH 4.5.

24. The method of claim 23, wherein the composition comprises a coating selected from the group consisting of polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters.

25. The method of claim 1 or 16, wherein the administering results in improvement in liver fibrosis, wherein the administering results in a reduction in fat content of liver, wherein the administering results in a reduction in the incidence of or progression of cirrhosis, wherein the administering results in a reduction in the incidence of hepatocellular carcinoma, wherein the administering results in a decrease in hepatic aminotransferase levels, wherein the administering results in a reduction in hepatic transaminase of between approximately 10% to 40%, wherein the administering results in a reduction in alanine aminotransferase levels in a treated patient to approximately 30%, 20% or 10% above normal ALT levels, or at normal ALT levels (≥40 iu/L), wherein the administering results in a reduction in aspartate aminotransferase levels in a treated patient to approximately 30%, 20% or 10% above normal AST levels or to normal AST levels, and/or wherein the administering results in a reduction in serum ferritin levels.

26. The method of claim 1 or 16, wherein the cysteamine or cystamine is administered with a second agent useful to treat fatty liver disease.

27. The method of claim 26, wherein the second agent is selected from a statin, a metformin, an antibody against oxidized phospholipids and any combination thereof.

* * * * *